(12) United States Patent
Thom et al.

(10) Patent No.: US 11,672,596 B2
(45) Date of Patent: Jun. 13, 2023

(54) ENERGY DELIVERY DEVICES WITH FLEXIBLE AND ADJUSTABLE TIPS

(71) Applicant: NeuWave Medical, Inc., Madison, WI (US)

(72) Inventors: Mark Thom, Madison, WI (US); Richard Schefelker, Madison, WI (US)

(73) Assignee: NeuWave Medical, Inc., Madison, WI (US)

( * ) Notice: Subject to any disclaimer, the term of this patent is extended or adjusted under 35 U.S.C. 154(b) by 511 days.

(21) Appl. No.: 16/259,531

(22) Filed: Jan. 28, 2019

(65) Prior Publication Data
US 2019/0262071 A1 Aug. 29, 2019

Related U.S. Application Data

(60) Provisional application No. 62/635,343, filed on Feb. 26, 2018.

(51) Int. Cl.
*A61B 18/18* (2006.01)
*A61B 18/14* (2006.01)
(Continued)

(52) U.S. Cl.
CPC ...... *A61B 18/1815* (2013.01); *A61B 18/1206* (2013.01); *A61B 18/14* (2013.01);
(Continued)

(58) Field of Classification Search
CPC . A61B 18/1206; A61B 18/14; A61B 18/1815; A61B 2018/00214;
(Continued)

(56) References Cited

U.S. PATENT DOCUMENTS 3,800,552 A 4/1974 Sollami
3,838,242 A 9/1974 Goucher
(Continued)

FOREIGN PATENT DOCUMENTS

AU 2015/202149 5/2015
CN 2579361 10/2003
(Continued)

OTHER PUBLICATIONS

Brace Christopher et al. "Analysis and experimental validation of a triaxial antenna for microwave tumor ablation" IEEE MTTS Int Microw Symp. Jun. 3, 2004(6-11) 1437-1440.
(Continued)

*Primary Examiner* — Michael F Peffley
(74) *Attorney, Agent, or Firm* — Casimir Jones, SC; Robert A. Goetz

(57) ABSTRACT

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, systems, devices, and methods are provided for treating a tissue region (e.g., a tumor) through application of energy using energy delivery devices with flexible and adjustable tips.

13 Claims, 2 Drawing Sheets

Figure 1:
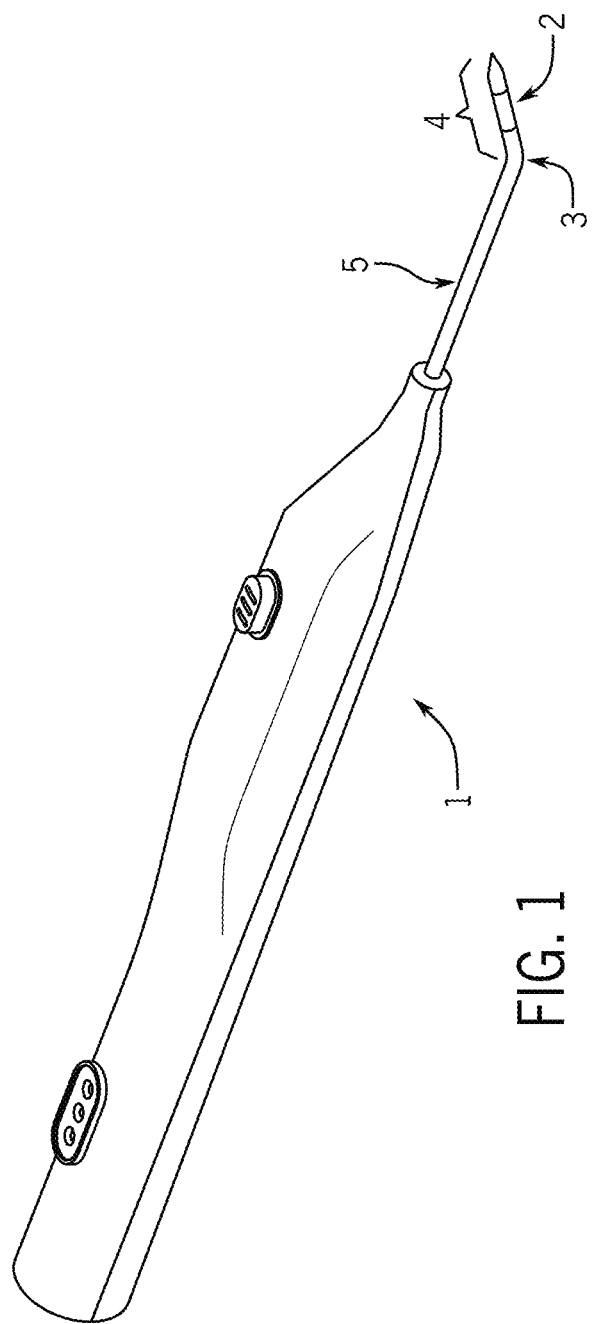

(51) Int. Cl.
*A61B 18/12* (2006.01)
*A61B 18/00* (2006.01)

(52) U.S. Cl.
CPC .............. *A61B 2018/0063* (2013.01); *A61B 2018/00214* (2013.01); *A61B 2018/00577* (2013.01); *A61B 2018/00589* (2013.01); *A61B 2018/00619* (2013.01); *A61B 2018/00702* (2013.01); *A61B 2018/00791* (2013.01); *A61B 2018/1405* (2013.01); *A61B 2018/1465* (2013.01); *A61B 2018/183* (2013.01); *A61B 2018/1861* (2013.01)

(58) Field of Classification Search
CPC A61B 2018/00577; A61B 2018/00589; A61B 2018/00619; A61B 2018/0063; A61B 2018/00702; A61B 2018/00791; A61B 2018/1405; A61B 2018/1465; A61B 2018/183; A61B 2018/1861
See application file for complete search history.

(56) References Cited

U.S. PATENT DOCUMENTS

| | | |
|---|---|---|
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr |
| 4,586,491 A | 5/1986 | Carpenter |
| 4,589,424 A | 5/1986 | Vaguine |
| 4,601,296 A | 7/1986 | Yerushalmi et al. |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,800,899 A | 1/1989 | Elliott et al. |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner et al. |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Stelzer |
| 5,129,396 A | 7/1992 | Rosen |
| 5,150,717 A | 9/1992 | Rosen |
| 5,167,619 A | 12/1992 | Wuchinich |
| 5,192,280 A * | 3/1993 | Parins ................ A61B 18/1485 606/48 |
| 5,211,625 A | 5/1993 | Sakurai |
| 5,213,561 A | 5/1993 | Weinstein et al. |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Milder |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,360,428 A * | 11/1994 | Hutchinson, Jr. .. A61B 18/1482 606/41 |
| 5,364,392 A | 11/1994 | Warner |
| 5,366,490 A | 11/1994 | Edwards |
| 5,368,592 A * | 11/1994 | Stern ................ A61M 25/0147 604/95.05 |
| 5,369,251 A | 11/1994 | King |
| 5,370,678 A | 12/1994 | Edwards |
| 5,405,346 A | 4/1995 | Grundy |
| 5,431,649 A | 7/1995 | Mulier |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell |
| 5,559,295 A | 9/1996 | Sheryll |
| 5,575,794 A | 11/1996 | Walus |
| 5,578,029 A | 11/1996 | Trelles |
| 5,591,227 A | 1/1997 | Dinh |
| 5,597,146 A | 1/1997 | Putman |
| 5,599,295 A | 2/1997 | Rosen |
| 5,599,352 A | 2/1997 | Dinh |
| 5,603,697 A | 2/1997 | Grundy |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt |
| 5,910,129 A * | 6/1999 | Koblish ............ A61M 25/0043 604/95.03 |
| 5,921,935 A | 7/1999 | Hickey |
| 5,957,969 A | 9/1999 | Warner |
| 5,963,082 A | 10/1999 | Dick |
| 5,995,875 A | 11/1999 | Blewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,066,132 A * | 5/2000 | Chen .................... A61B 18/08 604/530 |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |

(56) References Cited

U.S. PATENT DOCUMENTS

| | | | |
|---|---|---|---|
| 6,165,163 A | 12/2000 | Chien | |
| 6,174,307 B1 | 1/2001 | Daniel | |
| 6,182,666 B1 | 2/2001 | Dobak, III | |
| 6,188,930 B1 | 2/2001 | Carson | |
| 6,190,382 B1 | 2/2001 | Ormsby | |
| 6,208,903 B1 | 3/2001 | Richards | |
| 6,210,323 B1 | 4/2001 | Gilhuly | |
| 6,223,085 B1 | 4/2001 | Dann | |
| 6,230,060 B1 | 5/2001 | Mawhinney | |
| 6,231,571 B1* | 5/2001 | Ellman | A61B 18/1482 606/41 |
| 6,235,022 B1 | 5/2001 | Hallock | |
| 6,241,725 B1 | 6/2001 | Cosman | |
| 6,245,062 B1 | 6/2001 | Berube | |
| 6,246,784 B1 | 6/2001 | Summers | |
| 6,246,905 B1 | 6/2001 | Mogul | |
| 6,251,128 B1 | 6/2001 | Knopp | |
| 6,254,598 B1 | 7/2001 | Edwards | |
| 6,273,884 B1 | 8/2001 | Altshuler | |
| 6,273,885 B1 | 8/2001 | Koop | |
| 6,273,886 B1 | 8/2001 | Edwards | |
| 6,277,113 B1 | 8/2001 | Berube | |
| 6,287,302 B1 | 9/2001 | Berube | |
| 6,306,130 B1 | 10/2001 | Anderson | |
| 6,306,132 B1 | 10/2001 | Moorman | |
| 6,312,427 B1 | 11/2001 | Berube | |
| 6,325,796 B1* | 12/2001 | Berube | A61B 18/18 606/33 |
| 6,347,251 B1 | 2/2002 | Deng | |
| 6,355,033 B1 | 3/2002 | Moorman | |
| 6,364,876 B1 | 4/2002 | Erb | |
| 6,383,182 B1 | 5/2002 | Berube | |
| 6,395,803 B1 | 5/2002 | Angeletakis | |
| 6,398,781 B1 | 6/2002 | Goble | |
| 6,402,742 B1 | 6/2002 | Blewett | |
| 6,427,089 B1 | 7/2002 | Knowlton | |
| 6,435,872 B1 | 8/2002 | Nagel | |
| 6,461,351 B1 | 10/2002 | Woodruff | |
| 6,461,352 B2 | 10/2002 | Morgan | |
| 6,471,696 B1 | 10/2002 | Berube | |
| 6,500,174 B1 | 12/2002 | Maguire | |
| 6,506,189 B1 | 1/2003 | Rittman | |
| 6,514,249 B1 | 2/2003 | Maguire | |
| 6,524,308 B1 | 2/2003 | Muller | |
| 6,527,768 B2 | 3/2003 | Berube | |
| 6,530,922 B2 | 3/2003 | Cosman | |
| 6,546,077 B2 | 4/2003 | Chornenky | |
| 6,575,969 B1 | 6/2003 | Rittman, III et al. | |
| 6,577,903 B1 | 6/2003 | Cronin | |
| 6,582,426 B2 | 6/2003 | Moorman | |
| 6,582,486 B1 | 6/2003 | Delpiano | |
| 6,585,733 B2 | 7/2003 | Wellman | |
| 6,593,395 B2 | 7/2003 | Angeletakis | |
| 6,602,074 B1 | 8/2003 | Suh | |
| 6,622,731 B2 | 9/2003 | Daniel | |
| 6,635,055 B1 | 10/2003 | Cronin | |
| 6,638,277 B2 | 10/2003 | Schaefer et al. | |
| 6,652,520 B2 | 11/2003 | Moorman | |
| 6,663,625 B1 | 12/2003 | Ormsby | |
| 6,666,579 B2 | 12/2003 | Jensen | |
| 6,673,068 B1 | 1/2004 | Berube | |
| 6,683,625 B2 | 1/2004 | Muthusamy | |
| 6,694,163 B1 | 2/2004 | Vining | |
| 6,699,240 B2 | 3/2004 | Francischelli | |
| 6,702,576 B2 | 3/2004 | Fischer | |
| 6,709,271 B2 | 3/2004 | Yin | |
| 6,740,107 B2 | 5/2004 | Loeb | |
| 6,749,606 B2 | 6/2004 | Keast | |
| 6,752,767 B2 | 6/2004 | Turovskiy | |
| D493,531 S | 7/2004 | Padain | |
| 6,770,070 B1 | 8/2004 | Balbierz | |
| 6,780,178 B2 | 8/2004 | Palanker | |
| 6,802,840 B2* | 10/2004 | Chin | A61B 18/1492 606/41 |
| 6,817,976 B2 | 11/2004 | Rovegno | |
| 6,817,999 B2 | 11/2004 | Berube | |
| 6,823,218 B2 | 11/2004 | Berube | |
| 6,837,712 B2 | 1/2005 | Qian | |
| 6,847,848 B2 | 1/2005 | Sterzer | |
| 6,849,075 B2 | 2/2005 | Bertolero | |
| 6,852,091 B2 | 2/2005 | Edwards | |
| 6,866,624 B2 | 3/2005 | Chornenky | |
| 6,866,663 B2 | 3/2005 | Edwards | |
| 6,869,431 B2 | 3/2005 | Maguire et al. | |
| 6,878,147 B2 | 4/2005 | Prakash | |
| 6,890,968 B2 | 5/2005 | Angeletakis | |
| 6,893,436 B2 | 5/2005 | Woodard | |
| 6,898,454 B2 | 5/2005 | Atalar | |
| D507,649 S | 7/2005 | Padain | |
| 6,918,905 B2 | 7/2005 | Neuberger | |
| 6,924,325 B2 | 8/2005 | Qian | |
| 6,957,108 B2 | 10/2005 | Turner | |
| 6,962,586 B2 | 11/2005 | Berube | |
| 6,972,016 B2 | 12/2005 | Hill | |
| 6,976,986 B2 | 12/2005 | Berube | |
| 6,994,546 B2 | 2/2006 | Fischer | |
| 7,022,105 B1 | 4/2006 | Edwards | |
| 7,033,352 B1 | 4/2006 | Gauthier | |
| 7,097,641 B1 | 8/2006 | Arless | |
| 7,101,369 B2 | 9/2006 | Van der Weide | |
| 7,115,126 B2 | 10/2006 | Berube | |
| 7,128,739 B2 | 10/2006 | Prakash | |
| 7,142,633 B2 | 11/2006 | Eberhard | |
| 7,147,632 B2 | 12/2006 | Prakash | |
| 7,153,298 B1 | 12/2006 | Cohen | |
| 7,156,842 B2 | 1/2007 | Sartor | |
| 7,160,289 B2 | 1/2007 | Cohen | |
| 7,160,292 B2 | 1/2007 | Moorman | |
| 7,182,762 B2 | 2/2007 | Bortkiewicz | |
| 7,184,824 B2 | 2/2007 | Hashimshony | |
| 7,197,363 B2 | 3/2007 | Prakash | |
| 7,233,820 B2 | 6/2007 | Gilboa | |
| 7,244,254 B2 | 7/2007 | Brace | |
| 7,263,997 B2 | 9/2007 | Madsen | |
| 7,266,407 B2 | 9/2007 | Li et al. | |
| 7,282,049 B2 | 10/2007 | Orszulak | |
| 7,311,703 B2* | 12/2007 | Turovskiy | A61B 18/1815 606/33 |
| 7,318,824 B2 | 1/2008 | Prakash | |
| 7,324,104 B1 | 1/2008 | Bitter | |
| 7,331,960 B2 | 2/2008 | Schaer | |
| 7,381,208 B2 | 6/2008 | Van der Walt | |
| 7,400,929 B2 | 7/2008 | Zelickson et al. | |
| 7,402,140 B2 | 7/2008 | Spero | |
| 7,410,484 B2 | 8/2008 | Littrup | |
| 7,467,015 B2 | 12/2008 | Van der Weide | |
| 7,473,219 B1 | 1/2009 | Glenn | |
| 7,507,232 B1* | 3/2009 | Garito | A61B 18/148 606/15 |
| 7,527,623 B2 | 5/2009 | Prakash | |
| 7,594,313 B2 | 9/2009 | Prakash | |
| 7,601,149 B2 | 10/2009 | DiCarlo | |
| 7,625,369 B2 | 12/2009 | Abboud | |
| 7,722,620 B2 | 5/2010 | Truckai | |
| 7,731,677 B2 | 6/2010 | Sakurai | |
| 7,815,637 B2 | 10/2010 | Ormsby | |
| 7,826,904 B2 | 11/2010 | Appling | |
| 7,862,559 B2 | 1/2011 | Prakash | |
| 7,875,024 B2* | 1/2011 | Turovskiy | A61N 5/045 607/156 |
| 8,035,570 B2 | 10/2011 | Prakash | |
| 8,059,059 B2 | 11/2011 | Bonn | |
| 8,093,500 B2 | 1/2012 | Deborski | |
| 8,109,895 B2 | 2/2012 | Williams et al. | |
| 8,147,511 B2 | 4/2012 | Perry | |
| 8,152,799 B2 | 4/2012 | Ormsby | |
| 8,155,418 B2 | 4/2012 | Delso | |
| 8,235,981 B2 | 8/2012 | Prakash | |
| 8,357,148 B2 | 1/2013 | Boulais et al. | |
| 8,403,924 B2 | 3/2013 | Behnke | |
| 8,430,871 B2 | 4/2013 | Brannan | |
| 8,454,589 B2 | 6/2013 | Deno | |
| 8,515,554 B2 | 8/2013 | Carr | |
| 8,523,854 B2 | 9/2013 | Willyard | |

(56) References Cited

U.S. PATENT DOCUMENTS

| | | |
|---|---|---|
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide |
| 9,113,926 B2 | 8/2015 | Brannan |
| 9,119,649 B2 * | 9/2015 | van der Weide .. A61B 18/1815 |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |
| 9,456,736 B2 | 10/2016 | Onuki et al. |
| 9,895,143 B2 | 2/2018 | Inoue |
| 2001/0020166 A1 | 9/2001 | Daly et al. |
| 2001/0039416 A1 | 11/2001 | Moorman et al. |
| 2001/0049524 A1 | 12/2001 | Morgan et al. |
| 2002/0022836 A1 | 2/2002 | Goble |
| 2002/0026187 A1 | 2/2002 | Swanson et al. |
| 2002/0026188 A1 | 2/2002 | Balbierz et al. |
| 2002/0040185 A1 | 4/2002 | Atalar et al. |
| 2002/0072742 A1 | 6/2002 | Schaefer |
| 2002/0087151 A1 | 7/2002 | Mody |
| 2002/0087157 A1 | 7/2002 | Sliwa et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash |
| 2003/0120268 A1 | 6/2003 | Bertolero |
| 2003/0130711 A1 | 7/2003 | Pearson et al. |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 7/2004 | Sterzer |
| 2004/0158237 A1 | 8/2004 | Abboud |
| 2004/0186517 A1 | 9/2004 | Hill |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1 | 1/2005 | Turovskiy |
| 2005/0075629 A1 | 4/2005 | Chapelon |
| 2005/0107870 A1 | 5/2005 | Wang |
| 2005/0109900 A1 | 5/2005 | Schilt |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Weide |
| 2005/0245920 A1 | 11/2005 | Vitullo et al. |
| 2006/0064083 A1 | 3/2006 | Khalaj |
| 2006/0079886 A1 | 4/2006 | Orszulak et al. |
| 2006/0094956 A1 | 5/2006 | Vismanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch |
| 2006/0276780 A1 | 12/2006 | Brace |
| 2006/0289528 A1 | 12/2006 | Chiu |
| 2007/0016180 A1 | 1/2007 | Lee |
| 2007/0021741 A1 | 1/2007 | Marwan et al. |
| 2007/0066972 A1 | 3/2007 | Ormsby |
| 2007/0185554 A1 | 8/2007 | Appling |
| 2007/0203551 A1 | 8/2007 | Cronin |
| 2007/0208389 A1 | 9/2007 | Amundson et al. |
| 2007/0219546 A1 | 9/2007 | Mody et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn et al. |
| 2009/0281536 A1 | 11/2009 | Beckman et al. |
| 2009/0306644 A1 | 12/2009 | Mayse et al. |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0040300 A1 * | 2/2011 | Brannan ................ A61B 18/14 606/41 |
| 2011/0077635 A1 | 3/2011 | Bonn et al. |
| 2011/0098696 A1 | 4/2011 | Brannan |
| 2011/0118723 A1 | 5/2011 | Turner |
| 2011/0118725 A1 | 5/2011 | Mayse |
| 2011/0125145 A1 * | 5/2011 | Mody .................... A61B 18/18 606/33 |
| 2011/0213352 A1 | 9/2011 | Lee |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |

(56) References Cited

U.S. PATENT DOCUMENTS

| | | |
|---|---|---|
| 2012/0209257 A1 | 8/2012 | Weide et al. |
| 2012/0209261 A1 | 8/2012 | Mayse |
| 2012/0209296 A1 | 8/2012 | Mayse |
| 2012/0232544 A1 | 9/2012 | Willyard |
| 2012/0232549 A1 | 9/2012 | Willyard |
| 2012/0310228 A1 | 12/2012 | Bonn |
| 2012/0316551 A1 | 12/2012 | van der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham et al. |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1 | 10/2013 | Mallya et al. |
| 2013/0281851 A1 | 10/2013 | Carr |
| 2013/0306543 A1 | 11/2013 | Beisser |
| 2013/0338530 A1 | 12/2013 | Kassab |
| 2014/0005706 A1 | 1/2014 | Gelfand |
| 2014/0046174 A1 | 2/2014 | Ladtkow |
| 2014/0046176 A1 | 2/2014 | Ladtkow |
| 2014/0152656 A1 | 6/2014 | Yoo |
| 2014/0163664 A1 | 6/2014 | Goldsmith et al. |
| 2014/0276033 A1 | 9/2014 | Brannan |
| 2014/0276200 A1 | 9/2014 | Brannan |
| 2015/0080888 A1 | 3/2015 | Mueller |
| 2015/0148792 A1 | 5/2015 | Kim |
| 2015/0150628 A1 | 6/2015 | Buysse |
| 2015/0164587 A1 | 6/2015 | Bonn et al. |
| 2015/0190193 A1 | 7/2015 | Mayse |
| 2015/0250540 A1 | 9/2015 | Behdad |
| 2015/0351839 A1 | 12/2015 | Brannan |
| 2015/0374438 A1 | 12/2015 | van der Weide |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1723922 | 11/2006 |
| EP | 1723922 A | 11/2006 |
| EP | 2098184 | 9/2009 |
| EP | 2295000 | 3/2011 |
| EP | 2316370 | 5/2011 |
| EP | 1659969 | 10/2012 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| JP | 2013-052258 | 3/2013 |
| JP | 2015-024026 | 2/2015 |
| WO | WO 92/04934 | 4/1993 |
| WO | WO 93/09845 | 5/1993 |
| WO | WO 95/004385 | 9/1995 |
| WO | WO 97/48449 | 12/1997 |
| WO | WO 99/56643 | 11/1999 |
| WO | WO 00/57811 | 10/2000 |
| WO | WO 2000/057811 | 10/2000 |
| WO | WO 01/70114 | 9/2001 |
| WO | WO 03/039385 | 5/2003 |
| WO | WO 03/086498 | 10/2003 |
| WO | WO 03/088806 | 10/2003 |
| WO | WO 03/088858 | 10/2003 |
| WO | WO 2003/086190 | 10/2003 |
| WO | WO 2004/004586 | 1/2004 |
| WO | WO 04026122 | 1/2004 |
| WO | WO 04/033039 | 4/2004 |
| WO | WO 2004/084748 | 10/2004 |
| WO | WO 04/112628 | 12/2004 |
| WO | WO 2004/112628 | 12/2004 |
| WO | WO 2005/011049 | 2/2005 |
| WO | WO 05/034783 | 4/2005 |
| WO | WO 05/110265 | 11/2005 |
| WO | WO 06/002943 | 1/2006 |
| WO | WO 06/005579 | 1/2006 |
| WO | WO 06/008481 | 1/2006 |
| WO | WO 2006/002843 | 1/2006 |
| WO | WO 2006/004585 | 1/2006 |
| WO | WO 2006/084676 | 8/2006 |
| WO | WO 2006/12149 | 11/2006 |
| WO | WO 2006/122149 | 11/2006 |
| WO | WO 2006/127847 | 11/2006 |
| WO | WO 2007/076924 | 7/2007 |
| WO | WO 2007/112103 | 10/2007 |
| WO | WO 2008/008545 | 1/2008 |
| WO | WO 2008/044013 | 4/2008 |
| WO | WO 08/142686 | 11/2008 |
| WO | WO 2010/067360 | 6/2010 |
| WO | WO 11/008903 | 1/2011 |
| WO | WO 2011/017168 | 2/2011 |
| WO | 2011/143468 | 11/2011 |
| WO | WO 2011/140087 | 11/2011 |
| WO | WO 2013/173481 | 11/2013 |
| WO | 2014/008489 | 1/2014 |

OTHER PUBLICATIONS

Brace Christopher et al. "Microwave Ablation with a Triaxial Antenna: Results in ex vivo Bovine Liver" IEEE Transations on Microwave Theory and Techniques vol. 53 No. 1 Jan. 2005.
English translation of a Decision of Refusal from related Japanese Patent Application No. 2013-509179 dated Jun. 30, 2015.
European Search Report dated Mar. 3, 2009 EP Patent Application No. 06 802 385.2.
Golio "The RF and microwave handbook" Edition: 2. Published by CRC Press 2001 ISBN 0849338592X 97808493859626.
Head Hayden W. et al. "Thermal Ablation for Hepatocellular Carcinoma" Gastroenterology 2004:127:S167-S178.
International Search Report PCT/US06/031644 dated Aug. 17, 2007.
International Search Report PCT/US06/032811 dated Jan. 25, 2007.
International Search Report PCT/US2005/014534 dated Nov. 29, 2005.
International Search Report PCT/US2006/017981 dated Sep. 7, 2006.
International Search Report PCT/US2006/028821 dated Mar. 21, 2007.
International Search Report PCT/US2006/033341 dated Aug. 17, 2007.
Seki Toshihito et al. "Ultrasonically Guided Percutaneous Microwave Coagulation Therapy for Small Hepatocellular Carcinoma" Cancer Aug. 1, 1994 vol. 74 No. 3 pp. 817-825.

(56) References Cited

OTHER PUBLICATIONS

European Search Report, EP Patent Application No. 11778168, dated Oct. 2, 2013.
International Preliminary Report, PCT/US2007/007464, dated Sep. 30, 2008.
International Preliminary Report on Patentability, PCT/US2012/071310, dated Aug. 19, 2014.
International Preliminary Report on Patentability, PCT/US2011/035000, dated Nov. 6, 2012.
International Preliminary Report on Patentability, PCT/US2010/043558, dated Jan. 31, 2012.
Guy, AW(1971) IEEE Trans. Microwave Theory Tech. 19 pp. 205-214.
European Search Report, EP Patent Application No. 12860249.7, dated Sep. 15, 2015.
European Search Report, EP Patent Application No. 10806929.5, dated Feb. 21, 2013.
European Search Report, EP Patent Application No. 07810483, dated Mar. 22, 2013.
International Search Report, PCT/US2007/016082, dated Jul. 21, 2008.
International Search Report, PCT/US2011/035000, dated Jan. 6, 2012.
International Search Report, PCT/US2012/071310, dated Feb. 25, 2013.
International Preliminary Report, PCT/US2007/016082, dated Jan. 14, 2009.
"Carbon dioxide." Carbon dioxide—New World Encyclopedia. Web. <http://www.newworldencyclopedia.org/entry/Carbon_dioxide>.
International Patent Application No. PCT/US05/14534 dated Nov. 29, 2005.
International Search Report re: PCT/US16/58888 dated Feb. 15, 2017.
International Search Report re: PCT/US2016/058890 dated Jan. 19, 2017.
U.S. Appl. No. 09/847,181, filed May 1, 2001.
U.S. Appl. No. 10/370,179, filed Feb. 19, 2003.
U.S. Appl. No. 10/834,802, filed Apr. 29, 2004.
U.S. Appl. No. 10/961,761, filed Oct. 7, 2004.
U.S. Appl. No. 10/961,994, filed Oct. 7, 2004.
U.S. Appl. No. 10/980,699, filed Nov. 3, 2004.
U.S. Appl. No. 11/053,987, filed Feb. 8, 2005.
U.S. Appl. No. 11/236,985, filed Sep. 28, 2005.
U.S. Appl. No. 11/237,136, filed Sep. 28, 2005.
U.S. Appl. No. 11/237,430, filed Sep. 28, 2005.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
European Search Report, EP Patent Application No. 17168163.8, dated Sep. 13, 2017.
International Search Report & Written Opinion, International Patent Application No. PCT/US2017/027424, dated Oct. 9, 2017.
European Search Report dated Mar. 9, 2015, EP Patent Application No. 14189493.1.
Extended European Search Report, EP Patent Application No. 11778168 dated Sep. 24, 2013.
International Preliminary Report on Patentability re: PCT/US2007/007408 dated Sep. 30, 2008.
International Preliminary Report on Patentability re: PCT/US2016/058888 dated Dec. 11, 2017.
International Preliminary Report on Patentability re: PCT/US2016/058890 dated May 11, 2018.
International Search Report re: PCT/US2007/007408 dated Aug. 31, 2007.
Supplementary European Search Report dated May 20, 2019, EP Patent Application No. 16860697.8, 8 pages.
International Search Report and Written Opinion, International Patent Application No. PCT/IB2019/050965, dated Jun. 11, 2019, 15 pages.
International Preliminary Report on Patentability, International Patent Application No. PCT/IB2019/050965, dated Aug. 27, 2020, 8 pages.
Office Action, JP Patent Application No. 2020-544806, dated Feb. 7, 2023, 9 pages.

* cited by examiner

ENERGY DELIVERY DEVICES WITH FLEXIBLE AND ADJUSTABLE TIPS

FIELD OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, systems, devices, and methods are provided for treating a tissue region (e.g., a tumor) through application of energy using energy delivery devices with flexible and adjustable tips.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641, 649, 5,246,438, 5,405,346, 5,314,466, 5,800,494, 5,957,969, 6,471,696, 6,878,147, and 6,962,586).

Unfortunately, current devices configured to deliver radiofrequency or microwave energy have structural drawbacks. For example, radiofrequency, microwave and/or harmonic energy delivery devices typically have a number of different dedicated tools with different curved or formed tip shapes. Such a need for different shared tips is currently solved by offering a portfolio of tools for choice. But, such portfolio of tools may work for some scenarios but the inability to adjust the tip shape means that such shape is not always optimal.

As such, improved tips for energy delivery devices that can be formed to an optimal shape are needed.

The present invention addresses such needs.

SUMMARY OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy using energy delivery devices with flexible and adjustable tips. The flexible and adjustable tips of the ablation tools described herein provide the advantage of allowing the operator to customize the angle of the tip for specific locations and reducing the need for multiple different tools in a single procedure.

As such, in certain embodiments, the present invention provides energy delivery devices comprising: a) an antenna; and b) a conductive tip at a distal end of the antenna, wherein the conductive tip is constructed from a flexible and adjustable material. In some embodiments, the conductive tip is angled. In some embodiments, the conductive tip retains its shape during operation. In some embodiments, the conductive tip comprises a formable joint. In some embodiments, such devices are integrated into systems described herein and in U.S. Pat. No. 9,192,438, herein incorporated by reference in its entirety.

Such energy delivery devices are not limited to a particular type of antenna. In some embodiments, the antenna is any type of antenna capable of delivering energy (e.g., microwave energy, radiofrequency energy) with a flexible and adjustable conductive tip. In some embodiments, the antenna is an antenna that comprises an inner conductor. In some embodiments, the antenna is coaxial antenna. In some embodiments, the antenna is a triaxial antenna.

Similarly, in certain embodiments, the present invention provides energy delivery devices comprising an energy emission region, a main body, a flexible joint, and an adjustable tip. In some embodiments, the energy emission region is configured to emit ablation energy, the main body defines a main body linear axis of the energy delivery device, the flexible joint is positioned between the main body and the adjustable tip, the flexible joint is configured such that its direction in relation to the main body linear axis is adjustable in any desired direction and can be fixed at such a desired direction, and adjustment of the flexible joint results in identical adjustment of the adjustable tip.

Such energy delivery devices are not limited to a particular manner of adjustment for the flexible joint. In some embodiments, the flexible joint is configured such that its direction in relation to the main body linear axis is rotatably adjustable (e.g., manually or automatically) in any desired direction. In some embodiments, the flexible joint is configured such that its direction in relation to the main body linear axis is flexibly adjustable in any desired direction. In some embodiments, the flexible joint is configured such that its direction in relation to the main body linear axis is manually adjustable in any desired direction. In some embodiments, the flexible joint is configured such that its direction in relation to the main body linear axis is automatically adjustable in any desired direction.

Such energy delivery devices are not limited to a particular type of flexible joint. In some embodiments, the flexible joint is a formable joint. In some embodiments, the flexible joint is formed from a flexible and adjustable material.

In some embodiments, the energy emission region is configured to emit radiofrequency ablation energy. In some embodiments, the energy emission region is configured to emit microwave ablation energy. In some embodiments, the energy emission region comprises a microwave antenna. In some embodiments, the microwave antenna comprises a co-axial transmission line. In some embodiments, the microwave antenna comprises a tri-axial transmission line. In some embodiments, the microwave antenna extends entirely through the main body, the flexible joint, and the adjustable tip. In some embodiments, the microwave antenna extends entirely through the main body and the flexible joint, and partially through the adjustable tip. In some embodiments, the microwave antenna extends entirely through the main body and the flexible joint, and not through the adjustable tip. In some embodiments, the microwave antenna extends entirely through the main body and partially through the flexible joint, and not through the adjustable tip. In some embodiments, the microwave antenna extends entirely through the main body and not through the flexible joint and the adjustable tip.

In certain embodiments, the present invention provides systems comprising one or more of such energy delivery devices and, for example, a power supply electrically connected to the energy delivery device. In some embodiments, the power supply generates microwave energy.

In certain embodiments, the present invention provides methods for ablating a tissue region within a sample, comprising providing such an energy delivery device, adjusting the flexible joint to a desired direction in relation to the main body linear axis, positioning the energy delivery device to tissue region within the sample, and delivering energy from the energy delivery device to the tissue region within the sample under conditions such that the tissue region is ablated. In some embodiments, the sample is within a living subject. In some embodiments, the sample is within a living human subject.

Additional embodiments are described herein.

BRIEF DESCRIPTON OF THE DRAWINGS

FIG. 1 shows an exemplary energy delivery device having an adjustable tip.

Figure 2:
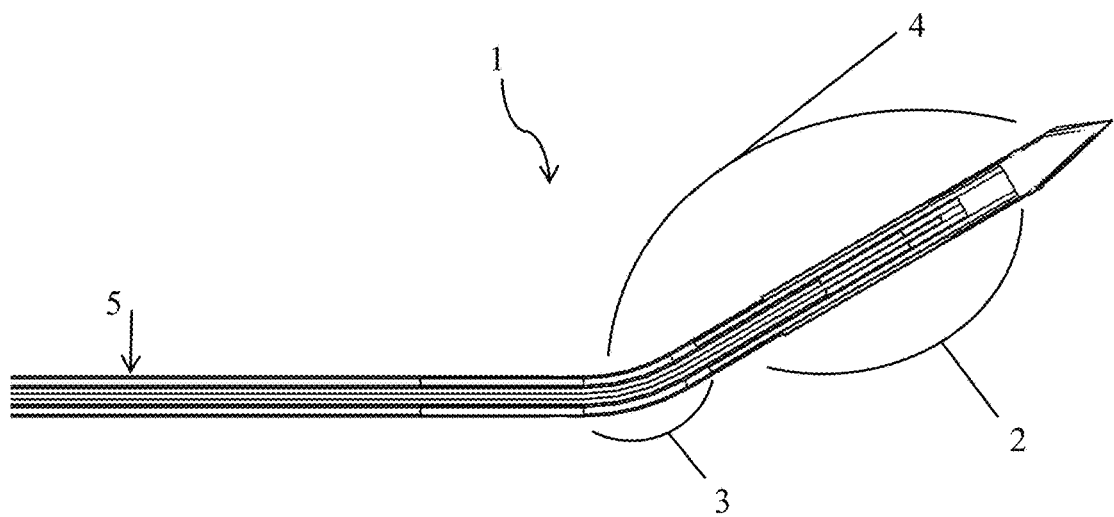
Figure 3:
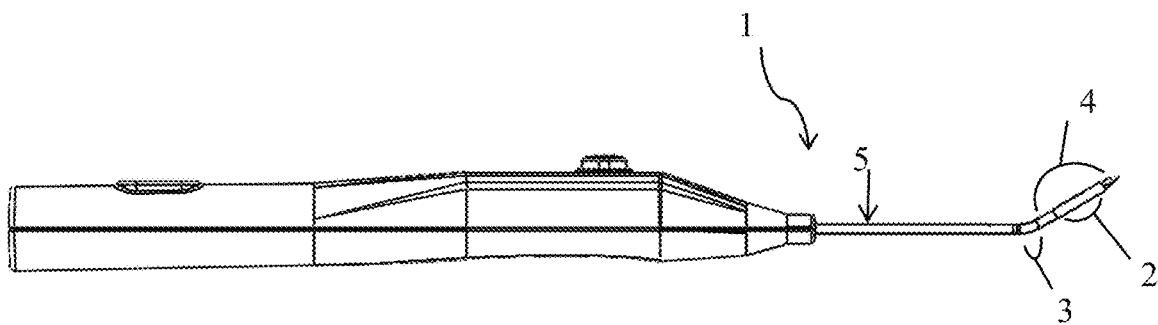

FIG. 2 and FIG. 3 each show energy delivery devices having an energy delivery device main body, an adjustable tip, an angled tip, and a flexible joint.

DETAILED DESCRIPTION

Currently used energy delivery device have tips that are rigid, and therefore difficult to manipulate or maneuver during a procedure involving ablation of a tissue region. As such, improved tips for energy delivery devices that can be formed to an optimal shape are needed. The present disclosure addresses this need by providing energy delivery devices having flexible and adjustable tips.

Accordingly, provided herein are energy delivery devices (e.g., for use in ablation procedures) comprising flexible and adjustable tips. In certain embodiments, the present invention provides energy delivery devices for use in ablation procedures comprising: a) an antenna; and b) a conductive tip at a distal end of the antenna, wherein the conductive tip is constructed from a flexible and adjustable material. In some embodiments, the conductive tip is angled. In some embodiments, the conductive tip retains its shape during operation. In some embodiments, the conductive tip comprises a formable joint. In some embodiments, such devices are integrated into systems described herein and in U.S. Pat. No. 9,192,438.

Such energy delivery devices comprising angled and adjustable tips provide advantages in use over devices with fixed tips. For example, users can adjust the angle of the tip during use and do not need to switch devices during a procedure. In addition, the completely customizable angle of the tip improves access to difficult to reach regions of the body or other target.

The present invention relates to comprehensive systems, devices and methods for delivering energy (e.g., microwave energy, radiofrequency energy) to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention provides systems for the delivery of energy (e.g., microwave energy) comprising a power supply, a means of directing, controlling and delivering power (e.g., a power splitter), a processor, an energy emitting device, a cooling system, an imaging system, a temperature monitoring system, and/or a tracking system. In certain embodiments, systems, devices, and methods are provided for treating a tissue region (e.g., a tumor) through use of the energy delivery systems of the present invention. In certain embodiments, systems, devices, and methods are provided for treating a tissue region (e.g., a tumor) through application of energy using ablation tools with flexible and adjustable tips.

The systems of the present invention may be combined within various system/kit embodiments. For example, the present invention provides systems comprising one or more of a generator, a power distribution system, a means of directing, controlling and delivering power (e.g., a power splitter), an energy applicator, along with any one or more accessory component (e.g., surgical instruments, software for assisting in procedure, processors, temperature monitoring devices, etc.). The present invention is not limited to any particular accessory component.

The systems of the present invention may be used in any medical procedure (e.g., percutaneous or surgical) involving delivery of energy (e.g., radiofrequency energy, microwave energy, laser, focused ultrasound, etc.) to a tissue region. The systems are not limited to treating a particular type or kind of tissue region (e.g., brain, liver, heart, blood vessels, foot, lung, bone, etc.). For example, the systems of the present invention find use in ablating tumor regions. Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors. In some embodiments, the surgical application comprises the control of hemorrhage (e.g. electrocautery). In some embodiments, the surgical application comprises tissue cutting or removal. In some embodiments, the device is configured for movement and positioning, with minimal damage to the tissue or organism, at any desired location, including but not limited to, the brain, neck, chest, abdomen, pelvis, and extremities. In some embodiments, the device is configured for guided delivery, for example, by computerized tomography, ultrasound, magnetic resonance imaging, fluoroscopy, and the like.

The illustrated embodiments provided below describe the systems and energy delivery devices having adjustable tips in terms of medical applications (e.g., ablation of tissue through delivery of microwave energy). However, it should be appreciated that such systems and devices of the present invention are not limited to medical applications. Such devices and systems may be used in any setting requiring delivery of energy to a load (e.g., agricultural settings, manufacture settings, research settings, etc.). The illustrated embodiments describe the devices and systems of the present invention in terms of microwave energy. It should be appreciated that the devices and systems of the present invention are not limited to a particular type of energy (e.g., radiofrequency energy, microwave energy, focused ultrasound energy, laser, plasma). As used herein, the terms "energy delivery device", "energy delivery device having an antenna", and "energy delivery devices having adjustable tips" are used interchangeably.

Systems of the present invention are not limited to any particular component or number of components. In some embodiments, the systems of the present invention include, but are not limited to including, a power supply, a means of directing, controlling and delivering power (e.g., a power splitter), a processor, an energy delivery device having an adjustable tip with an antenna, a cooling system, an imaging system, and/or a tracking system. When multiple antennas are in use, the system may be used to individually control each antenna separately.

In some embodiments, energy delivery devices having adjustable tips are provided as part of an energy delivery system comprising a device described herein, a power supply, a transmission line, a power distribution component (e.g., power splitter), a processor, an imaging system, and a temperature monitoring system. In some embodiments, the components of the energy delivery systems are connected via a transmission line, cables, etc. In some embodiments, the energy delivery device having an adjustable tip is separated from the power supply, a means of directing, controlling and delivering power (e.g., a power splitter), processor, imaging system, temperature monitoring system across a sterile field barrier.

FIG. 1 shows an exemplary energy delivery device 1 configured with an energy delivery device main body 5 and an adjustable tip 4 for improving manipulation and maneuvering of the energy delivery device during a procedure involving ablation of a tissue region. The energy delivery device 1 is not limited to a particular manner or configuration for improving manipulation and maneuvering of the energy delivery device during a procedure involving ablation of a tissue region.

Still referring to FIG. 1, in some embodiments, the energy delivery device 3 is configured to emit and/or deliver energy (e.g., ablation energy) (e.g., microwave ablation energy). Such energy delivery devices 1 are not limited to a particular region within the device that emits such energy. In some embodiments, the region of the energy delivery device 1 configured for energy emission is positioned entirely within the energy delivery device main body 5 and the adjustable tip 4. In some embodiments, the region of the energy delivery device 1 configured for energy emission is positioned within the entirety of the energy delivery device main body 5 and partially within (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) the adjustable tip 4. In some embodiments, the region of the energy delivery device 1 configured for energy emission is positioned within the entirety of the adjustable tip 4 and partially within the energy delivery device main body 5. In some embodiments, the region of the energy delivery device 3 configured for energy emission is positioned within a portion (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) of the adjustable tip 4 and within a portion (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) of the energy delivery device main body 5. In some embodiments, the region of the energy delivery device 1 configured for energy emission is entirely positioned within the adjustable tip 4 and not within the energy delivery device main body 5. In some embodiments, the region of the energy delivery device 1 configured for energy emission is entirely positioned within the energy delivery device main body 5 and not within the adjustable tip 4.

In some embodiments, the energy delivery device 1 has therein one or more antennae for such energy emission. Such energy delivery devices 1 are not limited to a particular positioning of the antenna. In some embodiments, the antenna(e) is positioned entirely within the energy delivery device main body 5 and the adjustable tip 4. In some embodiments, the antenna(e) is positioned within the entirety of the energy delivery device main body 5 and partially within (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) the adjustable tip 4. In some embodiments, the r antenna(e) is positioned within the entirety of the adjustable tip 4 and partially within the energy delivery device main body 5. In some embodiments, the antenna(e) is positioned within a portion (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) of the adjustable tip 4 and within a portion (e.g., 1%, 5%, 10%, 25%, 28%, 30%, 33%, 39%, 40%, 42%, 48%, 50%, 55%, 60%, 70%, 78%, 79%, 82%, 85%, 88%, 90%, 95%, 98%, 99%, 99.9%) of the energy delivery device main body 5. In some embodiments, the antenna(e) is entirely positioned within the adjustable tip 4 and not within the energy delivery device main body 5. In some embodiments, the antenna(e) is entirely positioned within the energy delivery device main body 5 and not within the adjustable tip 4.

Such embodiments of the present invention contemplate the use of any type of antenna for delivering (e.g., emitting) energy (e.g., ablation device, surgical device, etc.). Examples of applicable antennas include, but are not limited, to any of the antennas described in U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385. Such antenna include any and all medical, veterinary, and research application devices configured for energy emission, as well as devices used in agricultural settings, manufacturing settings, mechanical settings, or any other application where energy is to be delivered.

Referring again to FIG. 1, the adjustable tip 4 is not limited to a particular design or configuration. In some embodiments, the design and configuration of the adjustable tip 4 is such that the resulting energy delivery device 1 is capable of improved manipulation and maneuvering during a procedure involving ablation of a tissue region. In some embodiments, as shown in FIG. 1, the adjustable tip 4 includes an angled tip 2 connected to a flexible joint 3. In some embodiments, as shown in FIG. 1, the adjustable tip 4 is positioned at the distal end of the energy delivery device main body 5.

Still referring to FIG. 1, the energy delivery devices 1 are not limited to a particular type or configuration of the flexible joint 3. In some embodiments, as shown in FIG. 1, the flexible joint 3 is positioned between the energy delivery device main body 5 and the angled tip 2. In some embodiments, the flexible joint 3 has any type of configuration that renders the energy delivery device 3 capable of improved manipulation and maneuvering during a procedure involving ablation of a tissue region. As shown in FIG. 1, the energy delivery device main body 5 defines a central axis of the device as a whole.

Still referring to FIG. 1, in some embodiments, the flexible joint 3 is not limited to a particular direction or amount of flexibility. In some embodiments, the flexible joint 3 is configured to rotate in any direction in relation to the energy delivery device main body 5 and flex in any direction from such a rotated position. For example, in some embodiments, the flexible joint 3 is configured to rotate from 0 to 360 degrees in relation to the axis of the energy delivery device main body 5. In some embodiments, the flexible joint 3 is configured to flex from 0 to 360 degrees in relation to its rotated position. In some embodiments, the adjusted rotation and flexion position of the flexible joint 3 can be locked in such an adjusted position (e.g., such that when used in a procedure (e.g., delivery of ablation energy) the device retains the adjusted position). In some embodiments, the adjusted rotation and flexion position of the flexible joint 3 can be locked in such an adjusted position and, if desired, further adjusted.

Still referring to FIG. 1, the flexible joint 3 is not limited to a particular manner of adjustment. In some embodiments, a user (e.g., a physician, veterinarian, health care provider) can manually adjust the flexible joint 3 to a desired position prior to use in a procedure. In some embodiments, a user can automatically adjust the flexible joint 3 to a desired position (e.g., through use of software configured to adjust the flexible joint 3). In some embodiments, the flexible joint 3 can be adjusted during a procedure (e.g., manually or automatically).

Still referring to FIG. 1, the flexible joint 3 is not limited to a particular size. In some embodiments, the flexible joint 3 has any size that renders the energy delivery device 3 capable of improved manipulation and maneuvering during a procedure involving ablation of a tissue region.

Still referring to FIG. 1, the flexible joint 3 is not limited to a particular type or kind of joint. In some embodiments, the type of flexible joint 3 is any kind that renders the energy delivery device 3 capable of improved manipulation and maneuvering during a procedure involving ablation of a tissue region. In some embodiments, the flexible joint 3 is a formable joint.

FIGS. 2 and 3 show alternate embodiments of an energy delivery device 1 having an energy delivery device main body 5, an adjustable tip 4, an angled tip 2, and a flexible joint 3.

As noted, the systems utilize energy delivery devices having therein antennae configured to emit energy (e.g., microwave energy, radiofrequency energy, radiation energy). The systems are not limited to particular types or designs of antennae (e.g., ablation device, surgical device, etc.). In some embodiments, the systems utilize energy delivery devices having linearly shaped antennae (see, e.g., U.S. Pat. Nos. 6,878,147, 4,494,539, U.S. patent application Ser. Nos. 11/728,460, 11/728,457, 11/728,428, 10/961,994, 10/961,761; and International Patent Application No., WO 03/039385). In some embodiments, the systems utilize energy delivery devices having non-linearly shaped antennae (see, e.g., U.S. Pat. Nos. 6,251,128, 6,016,811, and 5,800,494, U.S. patent application Ser. No. 09/847,181, and International Patent Application No. WO 03/088858). In some embodiments, the antennae have horn reflection components (see, e.g., U.S. Pat. Nos. 6,527,768, 6,287,302). In some embodiments, the antenna has a directional reflection shield (see, e.g., U.S. Pat. No. 6,312,427). In some embodiments, the antenna has therein a securing component so as to secure the energy delivery device within a particular tissue region (see, e.g., U.S. Pat. Nos. 6,364,876, and 5,741,249).

Generally, antennae configured to emit energy comprise coaxial transmission lines. The devices are not limited to particular configurations of coaxial transmission lines. Examples of coaxial transmission lines include, but are not limited to, coaxial transmission lines developed by Pasternack, Micro-coax, and SRC Cables. In some embodiments, the coaxial transmission line has a center conductor, a dielectric element, and an outer conductor (e.g., outer shield). In some embodiments, the antennae have flexible coaxial transmission lines (e.g., for purposes of positioning around, for example, pulmonary veins or through tubular structures) (see, e.g., U.S. Pat. Nos. 7,033,352, 6,893,436, 6,817,999, 6,251,128, 5,810,803, 5,800,494). In some embodiments, the antennae have rigid coaxial transmission lines (see, e.g., U.S. Pat. No. 6,878,147, U.S. patent application Ser. Nos. 10/961,994, 10/961,761, and International Patent Application No. WO 03/039385).

In some embodiments, the energy delivery devices have a coaxial transmission line positioned within the antenna, and a coaxial transmission line connecting with the antenna. In some embodiments, the size of the coaxial transmission line within the antenna is larger than the coaxial transmission line connected with the antenna. The coaxial transmission line within the antenna and the coaxial transmission line connecting with the antenna are not limited to particular sizes. For example, in some embodiments, whereas the coaxial transmission line connected with the antenna is approximately 0.032 inches, the size of the coaxial transmission line within the antenna is larger than 0.032 inches (e.g., 0.05 inches, 0.075 inches, 0.1 inches, 0.5 inches). In some embodiments, the coaxial transmission line within the antenna has an inner conductor that is stiff and thick. In some embodiments, the end of the coaxial transmission line within the antenna is sharpened for percutaneous use. In some embodiments, the dielectric coating of the coaxial transmission line within the antenna is PTFE (e.g., for purposes of smoothing transitions from a cannula to an inner conductor (e.g., a thin and sharp inner conductor)).

Such embodiments are not limited to a particular coaxial transmission line shape. Indeed, in some embodiments, the shape of the coaxial transmission line and/or the dielectric element is selected and/or adjustable to fit a particular need.

In some embodiments, the outer conductor is a 20-gauge needle or a component of similar diameter to a 20-gauge needle. Preferably, for percutaneous use, the outer conductor is not larger than a 17-gauge needle (e.g., no larger than a 16-gauge needle). In some embodiments, the outer conductor is a 17-gauge needle. However, in some embodiments, larger devices are used, as desired. For example, in some embodiments, a 12-gauge diameter is used. The present invention is not limited by the size of the outer conductor. In some embodiments, the outer conductor is configured to fit within series of larger needles for purposes of assisting in medical procedures (e.g., assisting in tissue biopsy) (see, e.g., U.S. Pat. Nos. 6,652,520, 6,582,486, 6,355,033, 6,306,132). In some embodiments, the center conductor is configured to extend beyond the outer conductor for purposes of delivering energy to a desired location. In some embodiments, some or all of the feedline characteristic impedance is optimized for minimum power dissipation, irrespective of the type of antenna that terminates at its distal end.

In some embodiments, the energy delivery devices are provided with a proximal portion and a distal portion, wherein the distal portion is detachable and provided in a variety of different configurations that can attach to a core proximal portion. For example, in some embodiments, the proximal portion comprises a handle and an interface to other components of the system (e.g., power supply) and the distal portion comprises a detachable antenna having desired properties. A plurality of different antenna configured for different uses may be provided and attached to the handle unit for the appropriate indication.

In some embodiments, multiple (e.g., more than 1) (e.g., 2, 3, 4, 5, 10, 20, etc.) coaxial transmission lines and/or triaxial transmission lines are positioned within each energy delivery device for purposes of delivering high amounts of energy over an extended period of time.

In some embodiments, the energy delivery devices comprise a triaxial microwave probe with optimized tuning capabilities (see, e.g., U.S. Pat. No. 7,101,369; see, also, U.S. patent application Ser. Nos. 10/834,802, 11/236,985, 11/237,136, 11/237,430, 11/440,331, 11/452,637, 11/502,783, 11/514,628; and International Patent Application No. PCT/US05/14534). The triaxial microwave probes are not limited to particular optimized tuning capabilities. In some embodiments, the triaxial microwave probes have pre-defined optimized tuning capabilities specific for a particular tissue type. In some embodiments, triaxial microwave probes are configured to ablate a smaller tissue region (e.g., ablating only the edge of an organ, ablating a small tumor, etc.). In such embodiments, the length of the first conductor is decreased (e.g., such that the wire contacts the tip of the so as to retain a small ablation region).

In some embodiments, the devices of the present invention are configured to attach with a detachable handle. The present invention is not limited to a particular type of detachable handle. In some embodiments, the detachable handle is configured to connect with multiple devices (e.g., 1, 2, 3, 4, 5, 10, 20, 50 . . . ) for purposes of controlling the energy delivery through such devices. In some embodiments, the handle is designed with a power amplifier for providing power to an energy delivery device.

In some embodiments, the energy delivery devices having an adjustable tip are designed to physically surround a particular tissue region for purposes of energy delivery (e.g., the main body of the device and the adjustable tip may be flexibly shaped around a particular tissue region). For example, in some embodiments, the main body of the device and/or the adjustable tip may be flexibly shaped around a blood vessel (e.g., pulmonary vein) for purposes of delivering energy to a precise region within the tissue.

In some embodiments, energy delivery devices having an adjustable tip are configured to have main bodies with both flexible and inflexible regions. The energy delivery devices are not limited to particular configurations for main bodies having both flexible and inflexible regions. In some embodiments, the flexible regions comprise plastic (e.g., PEEK). In some embodiments, the inflexible regions comprise ceramic. The flexible and inflexible regions are not limited to particular positions within the main bodies of the energy delivery devices. In some embodiments, the flexible region is positioned in a region experiencing lower amounts of microwave field emission. In some embodiments, the inflexible region is positioned in a region experiencing high amounts of microwave field emission (e.g., located over the proximal portion of the antenna to provide dielectric strength and mechanical rigidity). In some embodiments, the energy delivery devices have a heat shrink over the distal portion (e.g., the antenna) for providing additional durability.

In some embodiments, the material of the antenna is durable and provides a high dielectric constant. In some embodiments, the material of the antenna is zirconium and/or a functional equivalent of zirconium. In some embodiments, the energy delivery devices having an adjustable tip are provided as two or more separate antenna attached to the same or different power supplies. In some embodiments, the different antennas are attached to the same handle, while in other embodiments different handles are provided for each antenna. In some embodiments, multiple antennae are used within a patient simultaneously or in series (e.g., switching) to deliver energy of a desired intensity and geometry within the patient. In some embodiments, the antennas are individually controllable. In some embodiments, the multiple antennas may be operated by a single user, by a computer, or by multiple users.

In some embodiments, the energy delivery devices having an adjustable tip are designed to operate within a sterile field. The present invention is not limited to a particular sterile field setting. In some embodiments, the sterile field includes a region surrounding a subject (e.g., an operating table). In some embodiments, the sterile field includes any region permitting access only to sterilized items (e.g., sterilized devices, sterilized accessory agents, sterilized body parts). In some embodiments, the sterile field includes any region vulnerable to pathogen infection. In some embodiments, the sterile field has therein a sterile field barrier establishing a barrier between a sterile field and a non-sterile field. The present invention is not limited to a particular sterile field barrier. In some embodiments, the sterile field barrier is the drapes surrounding a subject undergoing a procedure involving use of the energy delivery devices having adjustable tips of the present invention (e.g., tissue ablation). In some embodiments, a room is sterile and provides the sterile field. In some embodiments, the sterile field barrier is established by a user of the systems of the present invention (e.g., a physician). In some embodiments, the sterile field barrier hinders entry of non-sterile items into the sterile field. In some embodiments, the energy delivery device having an adjustable tip is provided in the sterile field, while one or more other components of the system (e.g., the power supply) are not contained in the sterile field.

In some embodiments, the energy delivery devices have therein protection sensors designed to prevent undesired use of the energy delivery devices having an adjustable tip. The energy delivery devices are not limited to a particular type or kind of protection sensors. In some embodiments, the energy delivery devices having an adjustable tip have therein a temperature sensor designed to measure the temperature of, for example, the energy delivery device and/or the tissue contacting the energy delivery device. In some embodiments, as a temperature reaches a certain level the sensor communicates a warning to a user via, for example, the processor. In some embodiments, the energy delivery devices having an adjustable tip have therein a skin contact sensor designed to detect contact of the energy delivery device with skin (e.g., an exterior surface of the skin). In some embodiments, upon contact with undesired skin, the skin contact sensor communicates a warning to a user via, for example, the processor. In some embodiments, the energy delivery devices having an adjustable tip have therein an air contact sensor designed to detect contact of the energy delivery device with ambient air (e.g., detection through measurement of reflective power of electricity passing through the device). In some embodiments, upon contact with undesired air, the skin contact sensor communicates a warning to a user via, for example, the processor. In some embodiments, the sensors are designed to prevent use of the energy delivery device (e.g., by automatically reducing or preventing power delivery) upon detection of an undesired occurrence (e.g., contact with skin, contact with air, undesired temperature increase/decrease). In some embodiments, the sensors communicate with the processor such that the processor displays a notification (e.g., a green light) in the absence of an undesired occurrence. In some embodiments, the sensors communicate with the processor such that the processor displays a notification (e.g., a red light) in the presence of an undesired occurrence and identifies the undesired occurrence.

In some embodiments, the energy delivery devices having an adjustable tip are used above a manufacturer's recommended power rating. In some embodiments, cooling techniques described herein are applied to permit higher power delivery. The present invention is not limited to a particular amount of power increase. In some embodiments, power ratings exceed manufacturer's recommendation by 5× or more (e.g., 5×, 6×, 10×, 15×, 20×, etc.).

In addition, the devices of the present invention are configured to deliver energy from different regions of the device (e.g., outer conductor segment gaps) at different times (e.g., controlled by a user) and at different energy intensities (e.g., controlled by a user). Such control over the device permits the phasing of energy delivery fields for purposes of achieving constructive phase interference at a particular tissue region or destructive phase interference at a particular tissue region. For example, a user may employ energy delivery through two (or more) closely positioned outer conductor segments so as to achieve a combined energy intensity (e.g., constructive phase interference). Such a combined energy intensity may be useful in particularly deep or dense tissue regions. In addition, such a combined energy intensity may be achieved through utilization of two (or more) devices. In some embodiments, phase interference (e.g., constructive phase interference, destructive phase interference), between one or more devices, is controlled by a processor, a tuning element, a user, and/or a power splitter. Thus, the user is able to control the release of energy through different regions of the device and control the amount of energy delivered through each region of the device for purposes of precisely sculpting an ablation zone.

The present invention provides a wide variety of methods for cooling the devices. Some embodiments employ meltable barriers that, upon melting, permit the contact of chemicals that carry out an endothermic reaction.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249. In some embodiments, the anchoring element has a circulating agent (e.g. a gas delivered at or near its critical point; $CO_2$) that freezes the interface between antenna and tissue thereby sticking the antenna in place. In some embodiments, as the tissue melts the antenna remains secured to the tissue region due to tissue desiccation.

Thus, in some embodiments, the devices of the present invention are used in the ablation of a tissue region having high amounts of air and/or blood flow (e.g., lung tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

In some embodiments, the energy delivery devices have therein a plug region designed to separate interior portion of the energy delivery device so as to, for example, prevent cooling or heating of a portion or portions of the device while permitting cooling or heating of other portions. The plug region may be configured to segregate any desired region or regions of an energy delivery device from any other. In some embodiments, the plug region is designed to prevent cooling of one or more regions of an energy delivery device. In some embodiments, the plug region is designed to prevent cooling of the portion of the energy delivery device configured to deliver ablative energy. The plug region is not limited to a particular manner of preventing cooling of a portion of the device. In some embodiments, the plug region is designed to be in contact with a region having a reduced temperature (e.g., a region of the energy delivery device having circulated coolant). In some embodiments, the material of the plug region is such that it is able to be in contact with a material or region having a low temperature without having its temperature significantly reduced (e.g., an insulating material). The plug region is not limited to a particular type of insulating material (e.g., a synthetic polymer (e.g., polystyrene, polyicynene, polyurethane, polyisocyanurate), aerogel, fibre-glass, cork). The plug region is not limited to particular size dimensions. In some embodiments, the size of the plug region is such that it is able to prevent the cooling effect of a circulating coolant from reducing the temperature of other regions of the energy delivery device. In some embodiments, the plug region is positioned along the entire cannula portion of an energy delivery device. In some embodiments, the plug region is positioned at a distal portion of the cannula portion of an energy delivery device. In some embodiments, the plug region wraps around the external portion of the cannula portion of an energy delivery device.

In some embodiments, the energy delivery devices have therein a "stick" region designed for securing the energy delivery device to a tissue region. The stick region is not limited to a particular manner of facilitating association of an energy delivery device to a tissue region. In some embodiments, the stick region is configured to attain and maintain a reduced temperature such that upon contact with a tissue region, the tissue region adheres to the stick region thereby resulting in attachment of the energy delivery device with the tissue region. The stick region is not limited to a particular material composition. In some embodiments, the stick region is, for example, a metal material, a ceramic material, a plastic material, and/or any combination of such substances. In some embodiments, the stick region comprises any kind of material able to attain and maintain a temperature such that upon contact with a tissue region induces adherence of the tissue region onto the stick region. The stick region is not limited to particular size dimensions. In some embodiments, the size of the stick region is such that it is able to maintain adherence of a tissue region during simultaneous tissue ablation and/or simultaneous movement (e.g., positioning) of the energy delivery device. In some embodiments, two or more stick regions are provided. In some embodiments, the stick region is prevented from exposure to the distal region of the device with a seal. In some embodiments, the seal is positioned between the stick region and the distal region of the device thereby preventing exposure of the stick region to the distal region.

In some embodiments, the seal is configured in an air/gas tight manner. In some embodiments, the seal is a laser welding onto the device (e.g., coaxial region). In some embodiments, the seal is induction soldered to the device (e.g., coaxial region). In some embodiments, the seal is partial (e.g., 60%/40%; 55%/45%; 50%/50%) laser welding and induction soldering. In some embodiments, the stick region is a part of (all or a portion) the adjustable tip. In some embodiments, the stick region is separate from the adjustable tip.

In some embodiments, the energy delivery devices having adjustable tips are configured for delivery of microwave energy with an optimized characteristic impedance (see, e.g., U.S. patent application Ser. No. 11/728,428). Such devices are configured to operate with a characteristic impedance higher than 50Ω. (e.g., between 50 and 90Ω; e.g., higher than 50, . . . , 55, 56, 57, 58, 59, 60, 61, 62, . . . 90Ω, preferably at 77Ω.).

In some embodiments, the energy delivery devices having adjustable tips have coolant passage channels (see, e.g., U.S. Pat. No. 6,461,351, and U.S. patent application Ser. No. 11/728,460). In particular, the energy delivery systems of the present invention utilize devices with coaxial transmission lines that allow cooling by flowing a cooling material through the dielectric and/or the inner or outer conductor of the coaxial component. In some embodiments, the devices are configured to minimize the diameter of the device, while permitting the passage of the coolant. This is accomplished, in some embodiments, by replacing strips of the inner or outer conductor and/or solid dielectric material with channels through which a coolant is transferred. In some embodiments, the channels are generated by stripping the outer or inner conductor and/or solid dielectric material along the length of the coaxial cable from one or more (e.g., two, three, four) zones. With the removed portions of the outer or inner conductor and/or solid dielectric material creating channels for transfer of the coolant, the stripped component fits within a smaller outer conductor than it did prior to removal of the outer or inner conductor and/or solid dielectric material. This provides for smaller devices with all of the advantages derived therefrom. In some embodiments where multiple channels are employed, coolant transfer may be in alternative directions through one or more of the channels. An advantage of such devices is that the diameter of the coaxial cable does not need to be increased to accommodate coolant. This permits the use of cooled devices that are minimally invasive and permit access to regions of a body that are otherwise inaccessible or accessible only with undesired risk. The use of coolant also permits greater energy delivery and/or energy deliver for prolonged periods of time.

In some embodiments, the energy delivery devices having adjustable tips employ a center fed dipole component (see, e.g., U.S. patent application Ser. No. 11/728,457). The devices are not limited to particular configurations. In some embodiments, the devices have therein a center fed dipole for heating a tissue region through application of energy (e.g., microwave energy). In some embodiments, such devices have a coaxial cable connected to a hollow tube (e.g., where the interior diameter is at least 50% of the exterior diameter; e.g., where the interior diameter is substantially similar to the exterior diameter). The coaxial cable may be a standard coaxial cable, or it may be a coaxial cable having therein a dielectric component with a near-zero conductivity (e.g., air). The hollow tube is not limited to a particular design configuration. In some embodiments, the hollow tube assumes the shape of (e.g., diameter of), for example, a 20-gauge needle. Preferably, the hollow tube is made of a solid, rigid conductive material (e.g., any number of metals, conductor-coated ceramics or polymers, etc.). In some embodiments, the hollow tube is configured with a sharpened point or the addition of a stylet on its distal end to permit direct insertion of the device into a tissue region without the use of, for example, a cannula. The hollow tube is not limited to a particular composition (e.g., metal, plastic, ceramic). In some embodiments, the hollow tube comprises, for example, copper or copper alloys with other hardening metals, silver or silver alloys with other hardening metals, gold-plated copper, metal-plated Macor (machinable ceramic), metal-plated hardened polymers, and/or combinations thereof. The stylet tip may be made of any material. In some embodiments, the tip is made from hardened resin. In some embodiments, the tip is metal. In some embodiments, the stylet tip is made from titanium or an equivalent of titanium. In some embodiments, the stylet tip is braised to zirconia or an equivalent of zirconia. In some such embodiments, the metal tip is an extension of a metal portion of an antenna and is electrically active.

In some embodiments, the energy delivery devices having adjustable tips have a linear array of antennae components (see, e.g., U.S. Provisional Patent Application No. 60/831, 055). The devices are not limited to particular configurations. In some embodiments, the energy delivery devices having a linear array of antennae components have therein an antenna comprising an inner conductor and an outer conductor, wherein the outer conductor is provided in two or more linear segments separated by gaps, such that the length and position of the segments is configured for optimized delivery of energy at the distal end of the antenna. For example, in some embodiments, an antenna comprises a first segment of outer conductor that spans the proximal end of the antenna to a region near the distal end and a second segment of outer conductor distal to the first segment wherein a gap separates or partially separates the first and second segments. The gaps may entirely circumscribe the outer conductor or may only partially circumscribe the outer conductor. In some embodiments, the length of the second segment is $\lambda/2$, $\lambda/4$, etc., although the present invention is not so limited. In some embodiments one or more additional (e.g., third, fourth, fifth) segments are provided distal to the second segment, each of which is separated from the other by a gap. In some embodiments, the antenna is terminated with a conductive terminal end that is in electronic communication with the inner conductor. In some embodiments, the conductive terminal end comprises a disc having a diameter substantially identical to the diameter of the outer conductor. Such antennae provide multiple peaks of energy delivery along the length of the distal end of the antenna, providing a broader region of energy delivery to target larger regions of tissue. The location and position of the peaks is controlled by selecting the length of the outer conductor segments and by controlling the amount of energy delivered.

In some embodiments, the energy delivery devices having adjustable tips have precision antennas or precision probes for coupling with an existing antenna.

The precision probes are not limited to coupling with a particular type of antenna. In some embodiments, the antenna has an inner conductor. In some embodiments, the antenna is a triaxial antenna (see, e.g., U.S. Pat. No. 7,101,369; see, also, U.S. patent application Ser. Nos. 10/834,802, 11/236,985, 11/237,136, 11,237,430, 11/440,331, 11/452,637, 11/502,783, 11/514,628; and International Patent Application No. PCT/US05/14534). In some embodiments, the antenna is a coaxial antenna. In some embodiments, the antenna is any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385)

The precision probes are not limited to a particular shape and/or design. In some embodiments, the shape of the precision probe is such that it is able to be fitted over the inner conductor of an antenna. In some embodiments, the shape and/or design of the precision probe is cylindrical. In some embodiments, the shape and/or design of the precision probe is tubular.

The precision probes are not limited to a particular positioning within an antenna. In some embodiments, so as to accommodate a precision probe, the outer conductor and dielectric of an antenna is removed so as to generate a portion along the inner conductor wherein the precision probe will be positioned (e.g., thereby generating an exposed inner conductor region). In some such embodiments, a precision probe is positioned along the entire exposed inner conductor region. In some such embodiments, an antenna sleeve (e.g., a polyfluorothetraethylene or PTFE antenna sleeve) is positioned along a portion of the exposed inner conductor and a precision probe positioned along the remaining portion of the exposed inner conductor.

The conductive fitting of the precision probes are not limited to a particular manner of coupling with the inner conductor of an antenna. In some embodiments, the fitting is soldered to an inner conductor. In some embodiments, the fitting is brazed to an inner conductor. In some embodiments, the fitting is crimped to an inner conductor. In some embodiments, the fitting is welded to an inner conductor. In some embodiments, the attachment between the precision probe and inner conductor is electrically conductive.

The precision probes are not limited to particular size dimensions. In some embodiments, the size dimensions of the precision probes are configured to accommodate any type or size of antenna (e.g., inner conductor or an antenna). In some embodiments, the diameter size of the precision probe is as large as possible so as to minimize impedance formed within an outer trocar cap.

In some embodiments, systems are providing which include one or more energy delivery devices having adjustable tips and processors that monitor and/or control and/or provide feedback concerning one or more of the components of the system. In some embodiments, the processor is provided within a computer module. The computer module may also comprise software that is used by the processor to carry out one or more of its functions. For example, in some embodiments, the systems of the present invention provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428). In some embodiments, the software is configured to provide information (e.g., monitoring information) in real time. In some embodiments, the software is configured to interact with the energy delivery systems of the present invention such that it is able to raise or lower (e.g., tune) the amount of energy delivered to a tissue region. In some embodiments, the software is designed to adjust the angle of the adjustable tip of the energy delivery device (see, FIG. 1 and accompanying description). In some embodiments, the software is designed to adjust the angle of the adjustable tip of the energy delivery device based upon detected condition changes during a procedure (e.g., changes in optimal tissue treatment region). In some embodiments, the software is designed to prime coolants for distribution into, for example, an energy delivery device such that the coolant is at a desired temperature prior to use of the energy delivery device. In some embodiments, the type of tissue being treated (e.g., liver) is inputted into the software for purposes of allowing the processor to regulate (e.g., tune) the delivery of microwave energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics. In some embodiments, the processor is operated by remote control.

In some embodiments, the processor is used to generate, for example, an ablation chart based upon entry of tissue characteristics (e.g., tumor type, tumor size, tumor location, surrounding vascular information, blood flow information, etc.). In such embodiments, the processor could direct placement of the energy delivery device so as to achieve desired ablation based upon the ablation chart.

In some embodiments a software package is provided to interact with the processor that allows the user to input parameters of the tissue to be treated (e.g., type of tumor or tissue section to be ablated, size, where it is located, location of vessels or vulnerable structures, and blood flow information) and then draw the desired ablation zone on a CT or other image to provide the desired results. The probes may be placed into the tissue, and the computer generates the expected ablation zone based on the information provided. Such an application may incorporate feedback. For example, CT, MRI, or ultrasound imaging or thermometry may be used during the ablation. This data is fed back into the computer, and the parameters readjusted to produce the desired result.

In some embodiments, user interface software is provided for monitoring and/or operating the components of the energy delivery systems. In some embodiments, the user interface software is operated by a touch screen interface. In some embodiments, the user interface software may be implemented and operated within a sterile setting (e.g., a procedure room) or in a non-sterile setting. In some embodiments, the user interface software is implemented and operated within a procedure device hub (e.g., via a processor). In some embodiments, the user interface software is implemented and operated within a procedure cart (e.g., via a processor). The user interface software is not limited to particular functions. Examples of functions associated with the user interface software include, but are not limited to, tracking the number of uses per component within the energy delivery system (e.g., tracking the number of times an energy delivery device is used), providing and tracking real time temperatures of each component or parts of each component (e.g., providing real time temperature of different locations along an energy delivery device (e.g., at the handle, at the stick, at the tip)) (e.g., providing real time temperature of the cables associated with the energy delivery systems), providing and tracking real time temperature of the tissue being treated, providing an automatic shut off for the part or all of the energy delivery system (e.g., an emergency shut off), generation of reports based upon the data accumulated, for example, prior to, during and after a procedure, providing audible and/or visual alerts to a user (e.g., alerts indicating a procedure has begun and/or is finished, alerts indicating a temperature has reached an aberrant level, alerts indicating the length of the procedure has gone beyond a default, etc.).

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP.RTM. disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks. As used herein, the terms "processor" and "central processing unit" or "CPU" are used interchangeably and refer to a device that is able to read a program from a computer memory device (e.g., ROM or other computer memory) and perform a set of steps according to the program.

In some embodiments, systems are provided including one or more energy delivery devices having adjustable tips and imaging systems comprising imaging devices. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697, 949, 5,603,697, and International Patent Application No. WO 06/005,579). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems provide software configured for use of imaging equipment (e.g., CT, MRI, ultrasound). In some embodiments, the imaging equipment software allows a user to make predictions based upon known thermodynamic and electrical properties of tissue, vasculature, and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the imaging systems of the present invention are used to monitor ablation procedures (e.g., microwave thermal ablation procedures, radio-frequency thermal ablation procedures). The present invention is not limited to a particular type of monitoring. In some embodiments, the imaging systems are used to monitor the amount of ablation occurring within a particular tissue region(s) undergoing a thermal ablation procedure. In some embodiments, the monitoring operates along with the ablation devices (e.g., energy delivery devices) such that the amount of energy delivered to a particular tissue region is dependent upon the imaging of the tissue region. The imaging systems are not limited to a particular type of monitoring. The present invention is not limited to what is being monitored with the imaging devices. In some embodiments, the monitoring is imaging blood perfusion for a particular region so as to detect changes in the region, for example, before, during and after a thermal ablation procedure. In some embodiments, the monitoring includes, but is not limited to, MRI imaging, CT imaging, ultrasound imaging, nuclear medicine imaging, and fluoroscopy imaging. For example, in some embodiments, prior to a thermal ablation procedure, a contrast agent (e.g., iodine or other suitable CT contrast agent; gadolinium chelate or other suitable MRI contrast agent, microbubbles or other suitable ultrasound constrast agent, etc.) is supplied to a subject (e.g., a patient) and the contrast agent perfusing thorugh a particular tissue region that is undergoing the ablation procedure is monitored for blood perfusion changes. In some embodiments, the monitoring is qualitative information about the ablation zone properties (e.g., the diameter, the length, the cross-sectional area, the volume). The imaging system is not limited to a particular technique for monitoring qualitative information. In some embodiments, techniques used to monitor qualitative information include, but are not limited to, non-imaging techniques (e.g., time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices). In some embodiments, the interstitial device provides a signal and/or detection for imaging (e.g., electro-acoustic imaging, electromagnetic imaging, electrical impedance tomography). In some embodiments, non-imaging techniques are used to monitor the dielectric properties of the medium surrounding the antenna, detect an interface between the ablated region and normal tissue through several means, including resonance frequency detection, reflectometry or distance-finding techniques, power reflection/transmission from interstitial antennas or external antennas, etc. In some embodiments, the qualitative information is an estimate of ablation status, power delivery status, and/or simple go/no-go checks to ensure power is being applied.

In some embodiments, the imaging systems are designed to automatically monitor a particular tissue region at any desired frequency (e.g., per second intervals, per one-minute intervals, per ten-minute intervals, per hour-intervals, etc.). In some embodiments, the present invention provides software designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the energy delivery devices. Likewise, an algorithm may be applied to predict the shape and size of the tissue region to be ablated (e.g., tumor shape) such that the system recommends the type, number, and location of ablation probes to effectively treat the region. In some embodiments, the system is configured to with a navigation or guidance system (e.g., employing triangulation or other positioning routines) to assist in or direct the placement of the probes and their use.

For example, such procedures may use the enhancement or lack of enhancement of a contrast material bolus to track the progress of an ablation or other treatment procedure. Subtraction methods may also be used (e.g., similar to those used for digital subtraction angiography). For example, a first image may be taken at a first time point. Subsequent images subtract out some or all of the information from the first image so that changes in tissue are more readily observed. Likewise, accelerated imaging techniques may be used that apply "under sampling" techniques (in constrast to Nyquist sampling). It is contemplated that such techniques provide excellent signal-to-noise using multiple low resolutions images obtained over time. For example, an algorithm called HYPER (highly constrained projection reconstruction) is available for MRI that may be applied to embodiments of the systems of the invention.

As thermal-based treatments coagulate blood vessels when tissue temperatures exceed, for example, 50° C., the coagulation decreases blood supply to the area that has been completely coagulated. Tissue regions that are coagulated do not enhance after the administration of contrast. In some embodiments, the present invention utilizes the imaging systems to automatically track the progress of an ablation procedure by giving, for example, a small test injection of contrast to determine the contrast arrival time at the tissue region in question and to establish baseline enhancement. In some embodiments, a series of small contrast injections is next performed following commencement of the ablation procedure (e.g., in the case of CT, a series of up to fifteen 10 ml boluses of 300 mgI/ml water soluble contrast is injected), scans are performed at a desired appropriate post-injection time (e.g., as determined from the test injection), and the contrast enhancement of the targeted area is determined using, for example, a region-of-interest (ROI) to track any one of a number of parameters including, but not limited to, attenuation (Hounsfield Units [HU]) for CT, signal (MRI), echogenicity (ultrasound), etc. The imaged data is not limited to a particular manner of presentation. In some embodiments, the imaging data is presented as color-coded or grey scale maps or overlays of the change in attenuation/signal/echogenicity, the difference between targeted and non-targeted tissue, differences in arrival time of the contrast bolus during treatment, changes in tissue perfusion, and any other tissue properties that can be measured before and after the injection of contrast material. The methods of the present invention are not limited to selected ROI's, but can be generalized to all pixels within any image. The pixels can be color-coded, or an overlay used to demonstrate where tissue changes have occurred and are occurring. The pixels can change colors (or other properties) as the tissue property changes, thus giving a near real-time display of the progress of the treatment. This method can also be generalized to 3d/4d methods of image display.

In some embodiments, the area to be treated is presented on a computer overlay, and a second overlay in a different color or shading yields a near real-time display of the progress of the treatment. In some embodiments, the presentation and imaging is automated so that there is a feedback loop to a treatment technology (RF, MW, HIFU, laser, cryo, etc) to modulate the power (or any other control parameter) based on the imaging findings. For example, if the perfusion to a targeted area is decreased to a target level, the power could be decreased or stopped. For example, such embodiments are applicable to a multiple applicator system as the power/time/frequency/duty cycle, etc. is modulated for each individual applicator or element in a phased array system to create a precisely sculpted zone of tissue treatment. Conversely, in some embodiments, the methods are used to select an area that is not to be treated (e.g., vulnerable structures that need to be avoided such as bile ducts, bowel, etc.). In such embodiments, the methods monitor tissue changes in the area to be avoided, and warn the user (e.g., treating physician) using alarms (e.g., visible and/or audible alarms) that the structure to be preserved is in danger of damage. In some embodiments, the feedback loop is used to modify power or any other parameter to avoid continued damage to a tissue region selected not to be treated. In some embodiments, protection of a tissue region from ablation is accomplished by setting a threshold value such as a target ROI in a vulnerable area, or using a computer overlay to define a "no treatment" zone as desired by the user.

In some embodiments, systems are provided including one or more energy delivery devices having adjustable tips and tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957,969, 5,405,346). In some embodiments, the device is pretuned to the desired tissue and is fixed throughout the procedure. In some embodiments, the tuning system is designed to match impedance between a generator and an energy delivery device (see, e.g., U.S. Pat. No. 5,364,392). In some embodiments, the tuning element is automatically adjusted and controlled by a processor of the present invention (see, e.g., U.S. Pat. No. 5,693,082). In some embodiments, a processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas or blood vessels, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

In some embodiments, systems are provided including one or more energy delivery devices having adjustable tips and coolant systems so as to reduce undesired heating within and along an energy delivery device (e.g., tissue ablation catheter). The systems of the present invention are not limited to a particular cooling system mechanism. In some embodiments, the systems are designed to circulate a coolant (e.g., air, liquid, etc.) throughout an energy delivery device such that the coaxial transmission line(s) and antenna (e) temperatures are reduced. In some embodiments, the systems utilize energy delivery devices having therein channels designed to accommodate coolant circulation. In some embodiments, the systems provide a coolant sheath wrapped around the antenna or portions of the antenna for purposes of cooling the antenna externally (see, e.g., U.S. patent application Ser. No. 11/053,987). In some embodiments, the systems utilize energy delivery devices having a conductive covering around the antenna for purposes of limiting dissipation of heat onto surrounding tissue (see, e.g., U.S. Pat. No. 5,358,515). In some embodiments, upon circulation of the coolant, it is exported into, for example, a waste receptacle. In some embodiments, upon circulation of the coolant it is recirculated. In some embodiments, the coolant is a gas circulated at or near its critical point. In some embodiments, the gas delivered at or near its critical point is carbon dioxide gas. In some embodiments, the energy delivery devices are configured to compress transported coolants (e.g., carbon dioxide gas at or near its critical point) at a desired pressure so as to retain the coolant at or near its critical point.

In some embodiments, the systems utilize expandable balloons in conjunction with energy delivery devices for purposes of urging tissue away from the surface of the antenna(e) (see, e.g., U.S. patent application Ser. No. 11/053,987).

In some embodiments, the systems utilize devices configured to attach onto an energy delivery device for purposes of reducing undesired heating within and along the energy delivery device (see, e.g., U.S. patent application Ser. No. 11/237,430).

In some embodiments, systems are provided including one or more energy delivery devices having adjustable tips and identification elements (e.g., RFID elements, identification rings (e.g., fidicials), barcodes, etc.) associated with one or more components of the system. In some embodiments, the identification element conveys information about a particular component of the system. The present invention is not limited by the information conveyed. In some embodiments, the information conveyed includes, but is not limited to, the type of component (e.g., manufacturer, size, energy rating, tissue configuration, etc.), whether the component has been used before (e.g., so as to ensure that non-sterile components are not used), the location of the component, patient-specific information and the like. In some embodiments, the information is read by a processor of the present invention. In some such embodiments, the processor configures other components of the system for use with, or for optimal use with, the component containing the identification element.

In some embodiments, the energy delivery devices have thereon one or more markings (e.g., scratches, color schemes, etchings (e.g., laser etchings), painted contrast agent markings, identification rings (e.g., fidicials), and/or ridges) so as to improve identification of a particular energy delivery device (e.g., improve identification of a particular device located in the vicinity of other devices with similar appearances). The markings find particular use where multiple devices are inserted into a patient. In such cases, particularly where the devices may cross each other at various angles, it is difficult for the treating physician to associate which proximal end of the device, located outside of the patient body, corresponds to which distal end of the device, located inside the patient body. In some embodiments, a marking (e.g., a number) a present on the proximal end of the device so that it is viewable by the physician's eyes and a second marking (e.g., that corresponds to the number) is present on the distal end of the device so that it is viewable by an imaging device when present in the body. In some embodiments, where a set of antennas is employed, the individual members of the set are numbered (e.g., 1, 2, 3, 4, etc.) on both the proximal and distal ends. In some embodiments, handles are numbered, a matching numbered detachable (e.g., disposable) antennas are connected to the handles prior to use. In some embodiments, a processor of the system ensures that the handles and antennas are properly matched (e.g., by RFID tag or other means). In some embodiments, where the antenna are disposable, the system provides a warning if a disposable component is attempted to be re-used, when it should have been discarded. In some embodiments, the markings improve identification in any type of detection system including, but not limited to, MRI, CT, and ultrasound detection.

The energy delivery systems of the present invention are not limited to particular types of tracking devices. In some embodiments, GPS and GPS related devices are used. In some embodiments, RFID and RFID related devices are used. In some embodiments, barcodes are used.

In such embodiments, authorization (e.g., entry of a code, scanning of a barcode) prior to use of a device with an identification element is required prior to the use of such a device. In some embodiments, the information element identifies that a components has been used before and sends information to the processor to lock (e.g. block) use of system until a new, sterile component is provided.

In some embodiments, systems are provided including one or more energy delivery devices having adjustable tips and temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately. In some embodiments, temperatures are monitored at several points along the antenna to estimate ablation status, cooling status or safety checks. In some embodiments, the temperatures monitored at several points along the antenna are used to determine, for example, the geographical characteristics of the ablation zone (e.g., diameter, depth, length, density, width, etc.) (e.g., based upon the tissue type, and the amount of power used in the energy delivery device). In some embodiments, the temperatures monitored at several points along the antenna are used to determine, for example, the status of the procedure (e.g., the end of the procedure). In some embodiments, temperature is monitored using thermocouples or electromagnetic means through the interstitial antenna.

The systems of the present invention (having one or more energy delivery devices having adjustable tips) may further employ one or more additional components that either directly or indirectly take advantage of or assist the features of the present invention. For example, in some embodiments, one or more monitoring devices are used to monitor and/or report the function of any one or more components of the system. Additionally, any medical device or system that might be used, directly or indirectly, in conjunction with the devices of the present invention may be included with the system. Such components include, but are not limited to, sterilization systems, devices, and components, other surgical, diagnostic, or monitoring devices or systems, computer equipment, handbooks, instructions, labels, and guidelines, robotic equipment, and the like.

In some embodiments, the systems employ pumps, reservoirs, tubing, wiring, and/or other components that provide materials on connectivity of the various components of the systems of the present invention. For example, any type of pump may be used to supply gas or liquid coolants to the antennas of the present invention. Gas or liquid handling tanks containing coolant may be employed in the system. In some embodiments, multiple tanks (e.g., 2, 3, 4, 5, 6, 7, 8, 9, 10, 20, 50, 100, etc.) are used simultaneously, in succession, or as needed. In some embodiments, more than one tank is used such that as one tank becomes empty, additional tanks will be used automatically so as to prevent a disruption in a procedure (e.g., as one $CO_2$ tank is drained empty, a second $CO_2$ tanks is used automatically thereby preventing procedure distruption). In some embodiments wherein $CO_2$ is employed, standard E sized $CO_2$ cylinders are used to supply $CO_2$.

In some embodiments, the systems employ one or more external heating devices. The systems are not limited to a particular use for external heating devices. In some embodiments, the external heating devices are used to retain certain elements of the system within a particular temperature range. For example, in some embodiments, external heating devices are used to retain gas or liquid handling tanks (e.g., tanks containing $CO_2$) providing coolant to one or more devices at within a particular temperature range. Indeed, in some embodiments, external heating devices prevent the natural decreasing in temperature a tank undergoes upon release of its contents thereby assuring that the coolant provided to the device is at a constant temperature or temperature range. The systems are not limited to particular external heating devices. The external heating devices are not limited to a particular manner of retaining the temperature within a particular range. In some embodiments, the external heating devices retain the pressure within a gas or liquid handling tanks (e.g., tanks containing $CO_2$) within a particular range (e.g., heating a tank containing $CO_2$ (e.g., a standard E sized $CO_2$ cylinder) at 1000 pounds per square inch so as to retain the pressure as it releases the $CO_2$ at 850 pounds per square.

In certain embodiments, the energy delivery systems (e.g., the energy delivery device having an adjustable tip, the processor, the power supply, the imaging system, the temperature adjustment system, the temperature monitoring system, and/or the identification systems) and all related energy delivery system utilization sources (e.g., cables, wires, cords, tubes, pipes providing energy, gas, coolant, liquid, pressure, and communication items) are provided in a manner that reduces undesired presentation problems (e.g., tangling, cluttering, and sterility compromise associated with unorganized energy delivery system utilization sources). The present invention is not limited to a particular manner of providing the energy delivery systems and energy delivery system utilization sources such that undesired presentation problems are reduced. In some embodiments, energy delivery systems and energy delivery system utilization sources organized with an import/export box, transport sheath, and procedure device pod provide several benefits. Such benefits include, but are not limited to, decreasing the number of cords traversing between a generator (e.g., a microwave generator) and a patient (e.g., decreasing the number of cords on the floor), de-cluttering the sterile environment and procedure room, increasing patient safety by having the energy delivery systems "move" with a patient thereby preventing device dislodgement (e.g., antenna dislodgement), increasing power delivery efficiency by reducing the energy travel distance within the energy delivery device, and reducing disposable costs by shortening the length of the disposable cables.

The present invention is not limited to a particular type or kind of import/export box. In some embodiments, the import/export box contains the power supply and coolant supply. In some embodiments, the import/export box is located outside of a sterile field in which the patient is being treated. In some embodiments, the import/export box is located outside of the room in which the patient is being treated. In some embodiments, the import/export box is located inside of the room in which the patient is being treated and maintained in a sterile manner. In some embodiments, one or more cables connect the import/export box to a procedure device pod. In some embodiments, a single cable is used (e.g., a transport sheath). For example, in some such embodiments, a transport sheath contains components for delivery of both energy and coolant to and/or from the import/export box. In some embodiments, the transport sheath connects to the procedure device pod without causing a physical obstacle for medical practitioners (e.g., travels under the floor, overhead, etc). In some embodiments, the cable is a low-loss cable (e.g., a low-loss cable attaching the power supply to the procedure device hub). In some embodiments, the low-loss cable is secured (e.g., to the procedure device hub, to a procedure table, to a ceiling) so as to prevent injury in the event of accidental pulling of the cable. In some embodiments, the cable connecting the power generator (e.g., microwave power generator) and the procedure device hub is low-loss reusable cable. In some embodiments, the cable connecting the procedure device hub to the energy delivery device is flexible disposable cable. In some embodiments, the cable connecting the procedure device hub to the energy delivery device has high flexibility with "memory" properties (e.g., the cable may be shaped to retain one or more desired positions). In some embodiments, the cable connecting the procedure device hub to the energy delivery device is a silicone covered fiberglass cable.

The present invention is not limited to a particular type or kind of procedure device pod. In some embodiments, the procedure device pod is configured to receive power, coolant, or other elements from the import/export box or other sources. In some embodiments, the procedure device pod provides a control center, located physically near the patient, for any one or more of: delivering energy to a medical device, circulating coolant to a medical device, collecting and processing data (e.g., imaging data, energy delivery data, safety monitoring data, temperature data, and the like), and providing any other function that facilitates a medical procedure. In some embodiments, the procedure device pod is configured to engage the transport sheath so as to receive the associated energy delivery system utilization sources. In some embodiments, the procedure device pod is configured to receive and distribute the various energy delivery system utilization sources to the applicable devices (e.g., energy delivery devices, imaging systems, temperature adjustment systems, temperature monitoring systems, and/or identification systems). For example, in some embodiments, the procedure device pod is configured to receive microwave energy and coolant from energy delivery system utilization sources and distribute the microwave energy and coolant to an energy delivery device. In some embodiments, the procedure device pod is configured to turn on or off, calibrate, and adjust (e.g., automatically or manually) the amount of a particular energy delivery system utilization source as desired. In some embodiments, the procedure device pod has therein a power splitter for adjusting (e.g., manually or automatically turning on, turning off, calibrating) the amount of a particular energy delivery system utilization source as desired. In some embodiments, the procedure device pod has therein software designed to provide energy delivery system utilization sources in a desired manner. In some embodiments, the procedure device pod has a display region indicating associated characteristics for each energy delivery system utilization source (e.g., which devices are presently being used/not used, the temperature for a particular body region, the amount of gas present in a particular $CO_2$ tank, etc.). In some embodiments, the display region has touch capability (e.g., a touch screen). In some embodiments, the processor associated with the energy delivery system is located in the procedure device pod. In some embodiments, the power supply associated with the energy delivery systems is located within the procedure device pod. In some embodiments, the procedure device pod has a sensor configured to automatically inhibit one or more energy delivery system utilization sources upon the occurrence of an undesired event (e.g., undesired heating, undesired leak, undesired change in pressure, etc.). In some embodiments, the weight of the procedure device hub is such that it could be placed onto a patient without causing discomfort and/or harm to the patient (e.g., less than 15 pounds, less than 10 pounds, less than 5 pounds).

The procedure device pods of the present invention are not limited to particular uses or uses within particular settings. Indeed, the procedure device pods are designed for use in any setting wherein the emission of energy is applicable. Such uses include any and all medical, veterinary, and research applications. In addition, the procedure device pods may be used in agricultural settings, manufacturing settings, mechanical settings, or any other application where energy is to be delivered. In some embodiments, the procedure device pods are used in medical procedures wherein patient mobility is not restricted (e.g., CT scanning, ultrasound imaging, etc.).

In some embodiments, the procedure device pod is designed for location within a sterile setting. In some embodiments, the procedure device pod is positioned on a patient's bed (e.g., on the bed; on a railing of the bed), a table that the patient is on (e.g., a table used for CT imaging, ultrasound imaging, MRI imaging, etc.), or other structure near the patient (e.g., the CT gantry). In some embodiments, the procedure device pod is positioned on a separate table. In some embodiments, the procedure device pod is attached to a ceiling. In some embodiments, the procedure device pod is attached to a ceiling such that a user (e.g., a physician) may move it into a desired position (thereby avoiding having to position the energy delivery system utilization sources (e.g., cables, wires, cords, tubes, pipes providing energy, gas, coolant, liquid, pressure, and communication items) on or near a patient while in use). In some embodiments, the procedure device hub is positioned to lay on a patient (e.g., on a patient's legs, thighs, waist, chest). In some embodiments, the procedure device hub is positioned above a patient's head or below a patient's feet. In some embodiments, the procedure device hub has Velcro permitting attachment onto a desired region (e.g., a procedure table, a patient's drape and/or gown).

In some embodiments, the procedure device hub is configured for attachment to a procedure strap used for medical procedures (e.g., a CT safety strap). In some embodiments, the procedure strap attaches to a procedure table (e.g., a CT table) (e.g., through a slot on the sides of the procedure table, through Velcro, through adhesive, through suction) and is used to secure a patient to the procedure table (e.g., through wrapping around the patient and connecting with, for example, Velcro). The procedure device hub is not limited to a particular manner of attachment with a procedure strap. In some embodiments, the procedure device hub is attached to the procedure strap. In some embodiments, the procedure device hub is attached to a separate strap permitting replacement of the procedure strap. In some embodiments, the procedure device hub is attached to a separate strap configured to attach to the procedure strap. In some embodiments, the procedure device hub is attached to a separate strap configured to attach to any region of the procedure table. In some embodiments, the procedure device hub is attached to a separate strap having insulation and/or padding to ensure patient comfort.

In some embodiments, the procedure device hub is configured for attachment to a procedure ring. The present invention is not limited to a particular type or kind of procedure ring. In some embodiments, the procedure ring is configured for placement around a patient (e.g., around a patient's torso, head, feet, arm, etc.). In some embodiments, the procedure ring is configured to attach to a procedure table (e.g., a CT table). The procedure device ring is not limited to a particular shape. In some embodiments, the procedure device ring is, for example, oval, circular, rectangular, diagonal, etc. In some embodiments, the procedure device ring is approximately half of a cyclical shape (e.g., 25% of a cyclical shape, 40% of a cyclical shape, 45% of a cyclical shape, 50% of a cyclical shape, 55 of a cyclical shape, 60 of a cyclical shape, 75 of a cyclical shape). In some embodiments, the procedure ring is, for example, metal, plastic, graphite, wood, ceramic, or any combination thereof. The procedure device hub is not limited to a particular manner of attachment to the procedure ring. In some embodiments, the procedure device hub attaches onto the procedure ring (e.g., with Velcro, with snap-ons, with an adhesive agent). In some embodiments utilizing low-loss cables, the low-loss cables additional attach onto the procedure ring. In some embodiments, the size of the procedure ring can be adjusted (e.g., retracted, extended) to accommodate the size of a patient. In some embodiments, additional items may be attached to the procedure ring. In some embodiments, the procedure ring may be easily moved to and from the vicinity of a patient.

In some embodiments, the procedure device hub is configured for attachment onto a custom sterile drape. The present invention is not limited to a particular type or kind of custom sterile drape. In some embodiments, the custom sterile drape is configured for placement onto a patient (e.g., onto a patient's torso, head, feet, arm, entire body, etc.). In some embodiments, the custom sterile drape is configured to attach to a procedure table (e.g., a CT table). The custom sterile drape is not limited to a particular shape. In some embodiments, the custom sterile drape is, for example, oval, circular, rectangular, diagonal, etc. In some embodiments, the shape of the custom sterile drape is such that it accommodates a particular body region of a patient. In some embodiments, the procedure ring is, for example, cloth, plastic, or any combination thereof. The procedure device hub is not limited to a particular manner of attachment to the custom sterile drape. In some embodiments, the procedure device hub attaches onto the custom sterile drape (e.g., with Velcro, with snap-ons, with an adhesive agent, clamps (e.g., alligator clamps)). In some embodiments utilizing low-loss cables, the low-loss cables additional attach onto the custom sterile drape. In some embodiments, additional items may be attached to the custom sterile drape. In some embodiments, the custom sterile drape may be easily moved to and from the vicinity of a patient. In some embodiments, the custom sterile drape has one more fenestrations for purposes of performing medical procedures.

In some embodiments, the procedure device hub is configured with legs for positioning the hub in the vicinity of a patient. In some embodiments, the procedure device hub has adjustable legs (e.g., thereby allowing positioning of the procedure device hub in a variety of positions). In some embodiments, the procedure device hub has three adjustable legs thereby allowing the device to be positioned in various tri-pod positions. In some embodiments, the legs have therein Velcro permitting attachment onto a desired region (e.g., a procedure table, a patient's drape and/or gown). In some embodiments, the legs are formed from a springy material configured to form an arc over the procedure table (e.g., CT table) and squeeze the rails of the procedure table. In some embodiments, the legs are configured to attach onto the rails of the procedure table.

In some embodiments, the procedure device pod is configured to communicate (wirelessly or via wire) with a processor (e.g., a computer, with the Internet, with a cellular phone, with a PDA). In some embodiments, the procedure device hub may be operated via remote control. In some embodiments, the procedure device pod has thereon one or more lights. In some embodiments, the procedure device hub provides a detectable signal (e.g., auditory, visual (e.g., pulsing light)) when power is flowing from the procedure device hub to an energy delivery device. In some embodiments, the procedure device hub has an auditory input (e.g., an MP3 player). In some embodiments, the procedure device hub has speakers for providing sound (e.g., sound from an MP3 player). In some embodiments, the procedure device hub has an auditory output for providing sound to an external speaker system. In some embodiments, the use of a procedure device pod permits the use of shorter cables, wires, cords, tubes, and/or pipes (e.g., less than 4 feet, 3 feet, 2 feet). In some embodiments, the procedure device pod and/or one or more components connected to it, or portions thereof are covered by a sterile sheath. In some embodiments, the procedure device hub has a power amplifier for supplying power (e.g., to an energy delivery device).

In some embodiments, the procedure device pod is configured to compress transported coolants (e.g., $CO_2$) at any desired pressure so as to, for example, retain the coolant at a desired pressure (e.g., the critical point for a gas) so as to improve cooling or temperature maintenance. For example, in some embodiments, a gas is provided at or near its critical point for the purpose of maintaining a temperature of a device, line, cable, or other component at or near a constant, defined temperature. In some such embodiments, a component is not cooled per se, in that its temperature does not drop from a starting temperature (e.g., room temperature), but instead is maintained at a constant temperature that is cooler than where the component would be, but for the intervention. For example, $CO_2$ may be used at or near its critical point (e.g., 31.1 Celsius at 78.21 kPa) to maintain temperature so that components of the system are sufficiently cool enough not to burn tissue, but likewise are not cooled or maintained significantly below room temperature or body temperature such skin in contact with the component freezes or is otherwise damaged by cold. Using such configurations permits the use of less insulation, as there are not "cold" components that must be shielded from people or from the ambient environment. In some embodiments, the procedure device pod has a retracting element designed to recoil used and/or unused cables, wires, cords, tubes, and pipes providing energy, gas, coolant, liquid, pressure, and/or communication items. In some embodiments, the procedure device pod is configured to prime coolants for distribution into, for example, an energy delivery device such that the coolant is at a desired temperature prior to use of the energy delivery device. In some embodiments, the procedure device pod has therein software configured to prime coolants for distribution into, for example, an energy delivery device such that the system is at a desired temperature prior to use of the energy delivery device. In some embodiments, the circulation of coolants at or near critical point permits cooling of the electronic elements of the energy delivery devices without having to use additional cooling mechanisms (e.g., fans).

In one illustrative embodiment, an import/export box contains one or more microwave power sources and a coolant supply (e.g., pressurized carbon dioxide gas). This import/export box is connected to a single transport sheath that delivers both the microwave energy and coolant to a procedure device pod. The coolant line or the energy line within the transport sheath may be wound around one another to permit maximum cooling of the transport sheath itself. The transport sheath is run into the sterile field where a procedure is to take place along the floor in a location that does not interfere with the movement of the medical team attending to the patient. The transport sheath connects to a table located near an imaging table upon which a patient lays. The table is portable (e.g., on wheels) and connectable to the imaging table so that they move together. The table contains arm, which may be flexible or telescoping, so as to permit positioning of the arm above and over the patient. The transport sheath, or cables connected to the transport sheath, run along the arm to the overhead position. At the end of the arm is the procedure device pod. In some embodiments, two or more arms are provided with two or more procedure device pods or two or more sub-components of a single procedure device pod. The procedure device pod is small (e.g., less than 1 foot cube, less than 10 cm cube, etc.) to allow easy movement and positioning above the patient. The procedure device pod contains a processor for controlling all computing aspects of the system. The device pod contains one or more connections ports for connecting cables that lead to energy delivery devices. Cables are connected to the ports. The cables are retractable and less than three feet in length. Use of short cables reduces expense and prevents power loss. When not in use, the cables hang in the air above the patient, out of contact with the patient's body. The ports are configured with a dummy load when not in use (e.g., when an energy delivery device is not connected to a particular port). The procedure device pod is within reach of the treating physician so that computer controls can be adjusted and displayed information can be viewed, in real-time, during a procedure.

In some embodiments, the energy delivery systems utilize procedure carts for maintaining system elements within one area. For example, in some embodiments, the systems provide a procedure cart that is configured to store the cooling supply (e.g., multiple tanks supplying gas or liquid coolant to the devices of the present invention) (e.g., standard E sized $CO_2$ cylinders) for device cooling purposes, external heating devices to maintain the coolant supply at desired pressures, one or more power supplies, one or more related energy delivery system utilization sources (e.g., cables, wires, cords, tubes, pipes providing energy, gas, coolant, liquid, pressure, and communication items), and/or the procedure device hub.

Indeed, the procedure cart is not limited to a particular design or purpose. In some embodiments, the procedure cart is configured for use within a sterile setting (e.g., a procedure room) and has therein cooling tanks, related external heating devices, and a procedure device pod/hub. In some embodiments, the procedure cart is configured for non-sterile settings only. In some embodiments, the procedure cart is configured for easy movement (e.g., it is designed with wheels). The procedure cart is configured to connect with any component of the energy delivery systems of the present invention (e.g., the import/export box, the transport sheath, and/or the procedure device hub). In some embodiments, the procedure cart has therein a display region for operating and/or monitoring the components of the energy delivery systems (e.g., user interface software). In some embodiments, the procedure cart is configured to communicate (wirelessly or via wire) with a processor (e.g., a computer, with the Internet, with a cellular phone, with a PDA). In some embodiments, the procedure cart is configured to send and receive information (wirelessly or via wire) pertaining to the energy delivery systems (e.g., the number of uses for each component, which devices are being used, etc.).

The systems of the present invention including energy delivery devices having adjustable tips are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the systems are configured for open surgery, percutaneous, intravascular, intracardiac, endoscopic, intraluminal, laparoscopic, or surgical delivery of energy. In some embodiments, the energy delivery devices may be positioned within a patient's body through a catheter, through a surgically developed opening, and/or through a body orifice (e.g., mouth, ear, nose, eyes, vagina, penis, anus) (e.g., a N.O.T.E.S. procedure). In some embodiments, the systems are configured for delivery of energy to a target tissue or region. In some embodiments, a positioning plate is provided so as to improve percutaneous, intravascular, intracardiac, laparoscopic, and/or surgical delivery of energy with the energy delivery systems of the present invention. The present invention is not limited to a particular type and/or kind of positioning plate. In some embodiments, the positioning plate is designed to secure one or more energy delivery devices at a desired body region for percutaneous, intravascular, intracardiac, laparoscopic, and/or surgical delivery of energy. In some embodiments, the composition of the positioning plate is such that it is able to prevent exposure of the body region to undesired heat from the energy delivery system. In some embodiments, the plate provides guides for assisted positioning of energy delivery devices. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising providing a tissue region and a system described herein (e.g., an energy delivery device having an adjustable tip, and at least one of the following components: a processor, a power supply, a temperature monitor, an imager, a tuning system, and/or a temperature reduction system); adjusting the adjustable tip to a desired angle and/or position in relation to the energy delivery device main body; positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. An energy delivery device comprising an energy emission region, a main body, a flexible joint, and an adjustable tip,
    wherein the energy emission region is configured to emit ablation energy, wherein the energy emission region comprises a microwave antenna, wherein the microwave antenna is configured to circulate a coolant,
    wherein the main body defines a main body linear axis of the energy delivery device,
    wherein the flexible joint is positioned between the main body and the adjustable tip,
    wherein the flexible joint is configured such that its direction in relation to the main body linear axis is adjustable in any desired direction and can be fixed at such a desired direction,
    wherein adjustment of the flexible joint results in identical adjustment of the adjustable tip,
    wherein the energy emission region is positioned entirely within the adjustable tip,
    wherein the energy emission region, the main body, the flexible joint, and the adjustable tip have a substantially uniform diameter.

2. The energy delivery device of claim 1, wherein the flexible joint is configured such that its direction in relation to the main body linear axis is rotatably adjustable in any desired direction.

3. The energy delivery device of claim 1, wherein the flexible joint is configured such that its direction in relation to the main body linear axis is flexibly adjustable in any desired direction.

4. The energy delivery device of claim 1, wherein the flexible joint is configured such that its direction in relation to the main body linear axis is manually adjustable in any desired direction.

5. The energy delivery device of claim 1, wherein the flexible joint is configured such that its direction in relation to the main body linear axis is automatically adjustable in any desired direction.

6. The energy delivery device of claim 1, wherein the flexible joint is a formable joint.

7. The energy delivery device of claim 1, wherein the flexible joint is formed from a flexible and adjustable material.

8. The energy delivery device of claim 1, wherein the energy emission region is configured to emit radiofrequency ablation energy.

9. The energy delivery device of claim 1, wherein the microwave antenna comprises a co-axial transmission line.

10. The energy delivery device of claim 1, wherein the microwave antenna comprises a tri-axial transmission line.

11. A system comprising the device of claim 1 and a power supply electrically connected to the energy delivery device.

12. The system of claim 11, wherein said power supply generates microwave energy.

13. A method of ablating a tissue region within a sample, comprising
    providing an energy delivery device of claim 1,
    adjusting the flexible joint to a desired direction in relation to the main body linear axis,
    positioning the energy delivery device to tissue region within the sample, wherein the sample is within a living human subject,
    delivering energy from the energy delivery device to the tissue region within the sample under conditions such that the tissue region is ablated.

* * * * *